US011643403B2

(12) United States Patent
Yoon et al.

(10) Patent No.: US 11,643,403 B2
(45) Date of Patent: May 9, 2023

(54) GLP-1 RECEPTOR AGONIST AND USE THEREOF

(71) Applicant: ILDONG PHARMACEUTICAL CO., LTD., Seoul (KR)

(72) Inventors: Hong Chul Yoon, Gyeonggi-do (KR); Kyung Mi An, Gyeonggi-do (KR); Myong Jae Lee, Gyeonggi-do (KR); Jin Hee Lee, Gyeonggi-do (KR); Jeong-geun Kim, Gyeonggi-do (KR); A-rang Im, Gyeonggi-do (KR); Woo Jin Jeon, Gyeonggi-do (KR); Jin Ah Jeong, Gyeonggi-do (KR); Jaeho Heo, Gyeonggi-do (KR); Changhee Hong, Gyeonggi-do (KR); Kyeojin Kim, Gyeonggi-do (KR); Jung-eun Park, Gyeonggi-do (KR); Te-ik Sohn, Gyeonggi-do (KR); Changmok Oh, Gyeonggi-do (KR); Da Hae Hong, Gyeonggi-do (KR); Sung Wook Kwon, Gyeonggi-do (KR); Jung Ho Kim, Gyeonggi-do (KR); Jae Eui Shin, Gyeonggi-do (KR); Yeongran Yoo, Gyeonggi-do (KR); Min Whan Chang, Gyeonggi-do (KR); Eun Hye Jang, Gyeonggi-do (KR); In-Gyu Je, Gyeonggi-do (KR); Ji Hye Choi, Gyeonggi-do (KR); Gunhee Kim, Gyeonggi-do (KR); Yearin Jun, Gyeonggi-do (KR)

(73) Assignee: ILDONG PHARMACEUTICAL CO., LTD., Seoul (KR)

( * ) Notice: Subject to any disclaimer, the term of this patent is extended or adjusted under 35 U.S.C. 154(b) by 0 days.

(21) Appl. No.: 17/777,193

(22) PCT Filed: Nov. 13, 2020

(86) PCT No.: PCT/KR2020/016019
§ 371 (c)(1),
(2) Date: May 16, 2022

(87) PCT Pub. No.: WO2021/096304
PCT Pub. Date: May 20, 2021

(65) Prior Publication Data
US 2023/0013143 A1 Jan. 19, 2023

(30) Foreign Application Priority Data

Nov. 15, 2019 (KR) .................. 10-2019-0146798
Feb. 24, 2020 (KR) .................. 10-2020-0022485

(51) Int. Cl.
| | |
|---|---|
| C07D 471/04 | (2006.01) |
| A61P 3/10 | (2006.01) |
| C07D 405/14 | (2006.01) |
| C07D 235/14 | (2006.01) |
| C07D 413/14 | (2006.01) |

(52) U.S. Cl.
CPC .............. *C07D 405/14* (2013.01); *A61P 3/10* (2018.01); *C07D 235/14* (2013.01); *C07D 413/14* (2013.01); *C07D 471/04* (2013.01)

(58) Field of Classification Search
CPC ................................ C07D 471/04; A61P 3/10
USPC .................................................... 514/253.04
See application file for complete search history.

(56) References Cited

U.S. PATENT DOCUMENTS

2021/0171499 A1  6/2021  Ammann et al.

FOREIGN PATENT DOCUMENTS

| | | |
|---|---|---|
| CN | 110325530 A | 10/2019 |
| KR | 10-2019-0094433 A | 8/2019 |
| TW | 202130630 A | 8/2021 |
| WO | WO-2008/012623 A1 | 1/2008 |
| WO | WO-2013/186229 A1 | 12/2013 |
| WO | WO-2015/086693 A1 | 6/2015 |
| WO | WO-2015/091531 A1 | 6/2015 |
| WO | 2018109607 * | 6/2018 |
| WO | WO-2018/109607 A1 | 6/2018 |

OTHER PUBLICATIONS

Office Action and English Translation from Taiwan Application No. 109139809 dated Aug. 17, 2022.
Written Opinion of the ISA in PCT/KR2020/016019, dated Feb. 25, 2021.
Notification of Reason for Refusal in KR 10-2020-0152019, with English translation, dated May 25, 2021.
Grant of Patent in KR 10-2020-0152019, with English translation, dated Nov. 22, 2021.
English Translation of Granted Claims in patent KR10-2344561.

* cited by examiner

*Primary Examiner* — Niloofar Rahmani
(74) *Attorney, Agent, or Firm* — Marshall, Gerstein & Borun LLP

(57) ABSTRACT

Disclosed are novel compounds of Chemical Formula 1, optical isomers of the compounds, and pharmaceutically acceptable salts of the compounds or the optical isomers. The compounds, isomers, and salts exhibit excellent activity as GLP-1 receptor agonists. In particular, they, as GLP-1 receptor agonists, exhibit excellent glucose tolerance, thus having a great potential to be used as therapeutic agents for metabolic diseases. Moreover, they exhibit excellent pharmacological safety for cardiovascular systems.

14 Claims, No Drawings

GLP-1 RECEPTOR AGONIST AND USE THEREOF

CROSS-REFERENCE TO RELATED APPLICATIONS

This is a U.S. National Phase of International Application PCT/KR2020/016019, filed Nov. 13, 2020, which claims priority to Korean Patent Application No. 10-2019-0146798, filed Nov. 15, 2019 and Korean Patent Application No. 10-2020-0022485, filed Feb. 24, 2020

TECHNICAL FIELD

The present application provides novel GLP-1R agonist compounds and uses of the compounds.

BACKGROUND ART

Insulin is a peptide secreted by beta cells of pancreas and is a substance that plays a very important role in regulating blood sugar in a body. Diabetes is a metabolic disease in which a concentration of glucose in the blood increases due to insufficient secretion of insulin or normal functioning thereof. A case in which blood sugar rises due to inability to secrete insulin from the pancreas is referred to as type 1 diabetes. Thus, administration of insulin is required to treat the type 1 diabetes. On the other hand, when insulin secretion is insufficient or the secreted insulin does not work properly and thus the blood sugar in the body is not controlled and rises, this is referred to as type 2 diabetes, which it is treated using a hypoglycemic agent based on a chemical substance.

It is well known based on large-scale clinical studies that strict blood sugar control toward a normal blood sugar level in diabetes treatment is important for preventing various complications caused by the diabetes.

A candidate compound that may lower the blood sugar by strongly stimulating the secretion of insulin includes a hormone referred to as glucagon like peptide-1 (GLP-1). GLP-1 was first discovered in 1985 as an incretin hormone secreted by L-cells in ileum and colon. GLP-1 increases insulin secretion by acting on a receptor referred to as GLP-1R (glucagon like peptide-1 receptor). GLP-1 is secreted via stimulation by absorbed nutrients or blood sugar levels. Diabetes treatment using GLP-1 has advantages that hypoglycemia does not occur because insulin is secreted depending on the glucose concentration. In addition, this hormone is known to be effective in reducing movement of an upper digestive system and suppressing appetite, and to proliferate existing beta cells of the pancreas.

Due to those characteristics thereof, GLP-1 was a candidate compound which was applied for a treatment method for the type 2 diabetes, but it had many obstacles in developing the same as a drug because a half-life in blood thereof was only 2 minutes. To overcome the shortcomings of GLP-1 due to the short action time, recently, therapeutic agents have been developed using a GLP-1 analog and a DPP-4 inhibitor which are resistant to an enzyme referred to as dipeptidyl peptidase IV (DPP-IV) that destroys the GLP-1 in the blood (Oh, SJ "Glucagon-like Peptide-1 Analogue and Dipeptidyl Peptidase-IV Inhibitors" Journal of the Korean Endocrine Society Vol. 21(6), pp. 437-447, 2006; Holst, J. J. "Glucagon like peptide 1: a newly discovered gastrointestinal hormone" Gastroenterology Vol. 107, pp. 1848-1855, 1994).

Among insulin-secreting peptides other than GLP-1, exendin is a peptide found in the salivary secretions of the Mexican beaded lizard (*Heroderma horridum*) and the Gila monster (*Helloderma suspectum*) as endogenous reptiles of Arizona and North Mexico. Exendin-3 is present in the salivary secretions of *Heroderma horridum*, and exendin-4 is present in the salivary secretions of *Helloderma suspectum*, and both have high homology with the GLP-1 sequence (Goke et al., J. Biol. Chem. Vol. 268, pp. 19650-19655, 1993). Pharmacological research reports state that exendin-4 may act on GLP-1 receptors on specific insulin-secreting cells, dispersed racemose gland cells from the pancreas of guinea pigs and stomach walls cells thereof. This peptide has been reported to stimulate somatostatin release and inhibit gastrin release from the isolated stomach.

Currently, various GLP-1 analogs having resistance to the DPP-4 enzyme that destroys GLP-1 in blood have been developed and are being used as a therapeutic agent for type 2 diabetes. These GLP-1 analogs have a considerably longer half-life compared to GLP-1, and thus they have the advantage of maintaining a hypoglycemic effect for a long time. However, oral administration thereof is not possible, resulting in low medication convenience in that they must be used in a form of an injection. Therefore, recently, research for discovering a small molecule GLP-1R agonist that may be administered orally and may be used as a diabetes treatment agent is being conducted. Recently, in Korea, it has been reported that DA-15864 as a novel small molecule compound that may selectively stimulate the GLP-1 receptor in humans and mice acts as a GLP-1 receptor agonist that may be administered orally to treat diabetes and obesity (Moon, H.-S. et al., "The development of non-peptide glucagon-like peptide 1 receptor agonist for the treatment of type 2 diabetes" Arch. Pharm. Res. Vol. 34(7), pp. 1041-1043, 2011). These oral formulations have high development value in that they act as GLP-JR agonists with improved easiness of administration.

Further, regulatory authorities such as US FDA are paying attention to cardiovascular side effects of drugs that may cause sudden death, especially QT prolongation and delayed ventricular repolarization. The pharmacological study of the cardiovascular safety of the novel substance is being emphasized. In this regard, human ether-a-go-go related gene (hERG) is a gene that encodes a subunit of the human potassium channels responsible for the delayed rectifier potassium current (IKr), which seems to have the most influential role in determining the duration of the action potential and thus the QT interval. If the hERG channel is inhibited by drugs, the ventricular repolarization determined by the duration of the cardiac action potential is delayed, an effect that can be measured as prolongation of the QT interval on the ECG. This has been associated with cardiotoxicity such as cardiac arrhythmia including Torsade de pointes (TdP). New pharmaceutical agent should be assessed in terms of inhibition of the hERG channels which have a significant impact on QT prolongation with regard to cardiovascular adverse events. In this process, most of the drugs have an effect on the inhibition of the hERG channels, and thus a development process thereof may stop.

Particularly, in the development of the diabetes treatment agents, QT prologation is an essential consideration. In the case of diabetes, the cause of death due to ischemic heart disease increased by 2 to 3 times or more. Women diagnosed with diabetes before age 30 are known to have a significant increased risk of myocardial infarction or fatal coronary artery disease. Thus, if an anti-diabetic drug causes the QT prolongation, it is difficult to develop the drug itself with an inevitable limitation for long-term use, even if it has an excellent effect.

DISCLOSURE

Technical Problem

There is thus a need for a new therapeutic agent. To meet the need, the present disclosure provides novel GLP-1 receptor agonist compounds that can significantly increase the activity of GLP-1 receptor from various candidate substances.

Technical Solution

In one aspect, the present disclosure provides compounds represented by the following Chemical Formula 1, optical isomers of the compounds, or pharmaceutically acceptable salts of the compounds or the optical isomers:

[Chemical Formula 1]

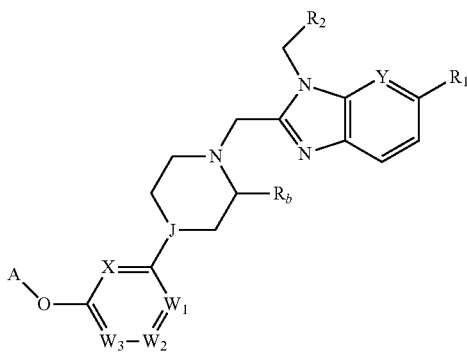

wherein $R_1$ is —C(=O)$R_a$, where $R_a$ is —OH or —O—($C_1$-$C_4$ alkyl);

Y is —CH— or —N—;

$R_2$ is one selected from the group consisting of substituted or unsubstituted $C_6$ to $C_{12}$ aryl, substituted or unsubstituted $C_5$ to $C_{12}$ heteroaryl, substituted or unsubstituted $C_3$ to $C_8$ heterocycloalkyl, substituted or unsubstituted $C_1$ to $C_4$ alkyl, and substituted or unsubstituted $C_3$ to $C_8$ cycloalkyl, where the substituted aryl, heteroaryl, heterocycloalkyl, alkyl, and cycloalkyl include at least one substitution with —OH, —($C_1$-$C_4$ alkyl), halogen, or —CN;

$R_b$ is hydrogen or —($C_1$-$C_4$ alkyl);

J is —CH— or —N—;

X is —$CR_c$— or —N—, where $R_c$ is one selected from the group consisting of —H, halogen, —CN, —OH, —O—($C_1$-$C_4$ alkyl), —$NH_2$, —$NO_2$, and —$C_1$-$C_4$ haloalkyl;

$W_1$ is —$CR_d$—, where $R_d$ is one selected from a group consisting of —H, halogen, —CN, —OH, —O—($C_1$-$C_4$ alkyl), —$NH_2$, —$NO_2$, and —$C_1$-$C_4$ haloalkyl;

$W_2$ is —$CR_e$— or —N—, where $R_e$ is one selected from a group consisting of —H, halogen, —CN, —OH, —O—($C_1$-$C_4$ alkyl), —$NH_2$, —$NO_2$, and —$C_1$-$C_4$ haloalkyl;

$W_3$ is —$CR_f$—, where $R_f$ is one selected from a group consisting of —H, halogen, —CN, —OH, —O—($C_1$-$C_4$ alkyl), —$NH_2$, —$NO_2$, and —$C_1$-$C_4$ haloalkyl; and A is

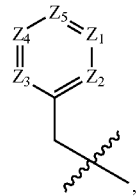

wherein:

$Z_1$ is —$CR_g$— or —N—, where $R_g$ is one selected from a group consisting of —H, halogen, —CN, —OH, —O—($C_1$-$C_4$ alkyl), —$NH_2$, —$NO_2$, and —$C_1$-$C_4$ haloalkyl;

$Z_2$ is —$CR_h$— or —N—, where $R_h$ is one selected from a group consisting of —H, halogen, —CN, —OH, —O—($C_1$-$C_4$ alkyl), —$NH_2$, —$NO_2$, and —$C_1$-$C_4$ haloalkyl;

$Z_3$ is —$CR_i$— or —N—, where $R_i$ is one selected from a group consisting of —H, halogen, —CN, —OH, —O—($C_1$-$C_4$ alkyl), —$NH_2$, —$NO_2$, and —$C_1$-$C_4$ haloalkyl;

$Z_4$ is —$CR_j$— or —N—, where $R_j$ is one selected from a group consisting of —H, halogen, —CN, —OH, —O—($C_1$-$C_4$ alkyl), —$NH_2$, —$NO_2$, and —$C_1$-$C_4$ haloalkyl;

$Z_5$ is —$CR_k$— or —N—, where $R_k$ is one selected from a group consisting of —H, halogen, —CN, —OH, —O—($C_1$-$C_4$ alkyl), —$NH_2$, —$NO_2$, and —$C_1$-$C_4$ haloalkyl; and $Z_1$ to $Z_5$ satisfy one of the following conditions:

i) at least one of $Z_1$ to $Z_5$ is —N—; and ii) $Z_1$ is —$CR_g$—, $Z_2$ is —$CR_h$—, $Z_3$ is —$CR_i$—, $Z_4$ is —$CR_j$—, $Z_5$ is —$CR_k$—, and wherein when $Z_1$ to $Z_5$ satisfy the condition ii),

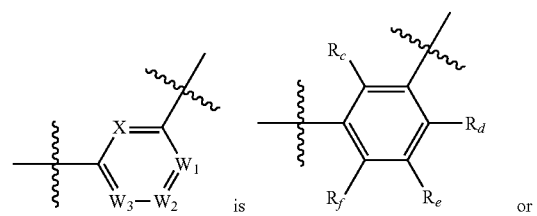

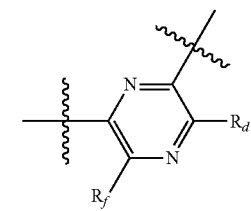

In another aspect, the present disclosure provides compounds represented by the following Chemical Formula 1, optical isomers of the compounds, or pharmaceutically acceptable salts of the compounds or the optical isomers:

[Chemical Formula 1]

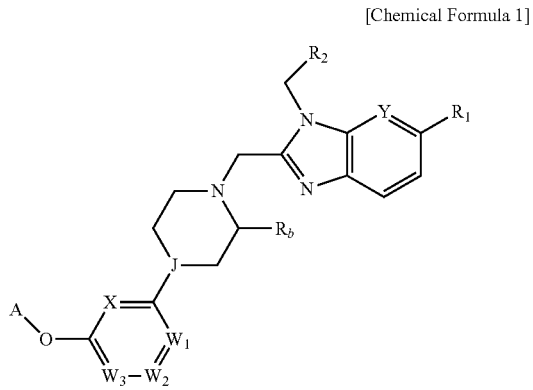

wherein $R_1$ is —C(=O)$R_a$, where $R_a$ is —OH or —O—($C_1$-$C_4$ alkyl);

Y is —CH— or —N—;

$R_2$ is one selected from the group consisting of substituted or unsubstituted $C_6$ to $C_{12}$ aryl, substituted or unsubstituted $C_5$ to $C_{12}$ heteroaryl, substituted or unsubstituted $C_3$ to $C_8$ heterocycloalkyl, substituted or unsubstituted $C_1$ to $C_4$ alkyl, and substituted or unsubstituted $C_3$ to $C_8$ cycloalkyl, where the substituted aryl, heteroaryl, heterocycloalkyl, alkyl and cycloalkyl include at least one substitution with —OH, —($C_1$-$C_4$ alkyl), halogen, or —CN;

$R_b$ is hydrogen or —($C_1$-$C_4$ alkyl);

J is —CH— or —N—;

X is —$CR_c$— or —N—, where $R_c$ is one selected from the group consisting of —H, halogen, —CN, —OH, —O—($C_1$-$C_4$ alkyl), —$NH_2$, —$NO_2$, and —$C_1$-$C_4$ haloalkyl;

$W_1$ is —$CR_d$—, where $R_d$ is one selected from a group consisting of —H, halogen, —CN, —OH, —O—($C_1$-$C_4$ alkyl), —$NH_2$, —$NO_2$, and —$C_1$-$C_4$ haloalkyl;

$W_2$ is —$CR_e$— or —N—, where $R_e$ is one selected from a group consisting of —H, halogen, —CN, —OH, —O—($C_1$-$C_4$ alkyl), —$NH_2$, —$NO_2$, and —$C_1$-$C_4$ haloalkyl;

$W_3$ is —$CR_f$—, where $R_f$ is one selected from a group consisting of —H, halogen, —CN, —OH, —O—($C_1$-$C_4$ alkyl), —$NH_2$, —$NO_2$, and —$C_1$-$C_4$ haloalkyl; and A is

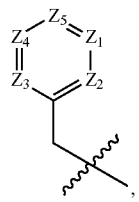

wherein:

$Z_1$ is —$CR_g$— or —N—, where $R_g$ is one selected from a group consisting of —H, halogen, —CN, —OH, —O—($C_1$-$C_4$ alkyl), —$NH_2$, —$NO_2$, and —$C_1$-$C_4$ haloalkyl;

$Z_2$ is —$CR_h$— or —N—, where $R_h$ is one selected from a group consisting of —H, halogen, —CN, —OH, —O—($C_1$-$C_4$ alkyl), —$NH_2$, —$NO_2$, and —$C_1$-$C_4$ haloalkyl;

$Z_3$ is —$CR_i$— or —N—, where $R_i$ is one selected from a group consisting of —H, halogen, —CN, —OH, —O—($C_1$-$C_4$ alkyl), —$NH_2$, —$NO_2$, and —$C_1$-$C_4$ haloalkyl;

$Z_4$ is —$CR_j$— or —N—, where $R_j$ is one selected from a group consisting of —H, halogen, —CN, —OH, —O—($C_1$-$C_4$ alkyl), —$NH_2$, —$NO_2$, and —$C_1$-$C_4$ haloalkyl;

$Z_5$ is —$CR_k$— or —N—, where $R_k$ is one selected from a group consisting of —H, halogen, —CN, —OH, —O—($C_1$-$C_4$ alkyl), —$NH_2$, —$NO_2$, and —$C_1$-$C_4$ haloalkyl; and $Z_1$ to $Z_5$ satisfy one of the following conditions:

i) at least one of $Z_1$ to $Z_5$ is —N—; and ii) $Z_1$ is —$CR_g$—, $Z_2$ is —$CR_h$—, $Z_3$ is —$CR_i$—, $Z_4$ is —$CR_j$—, $Z_5$ is —$CR_k$—, wherein

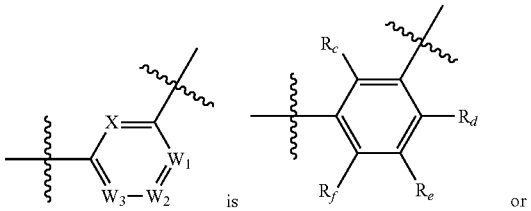

and wherein when

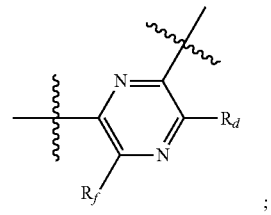

$R_b$ is —($C_1$-$C_4$ alkyl);

when

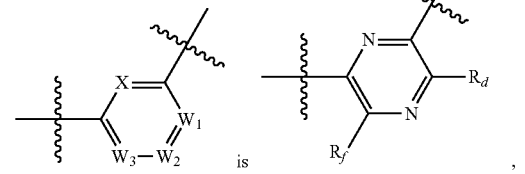

and J is —CH—, Y is —N—; and

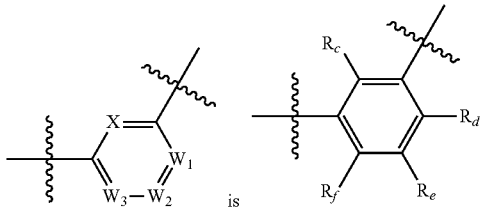 is and J is —N—, $R_2$ is substituted or unsubstituted $C_3$ to $C_8$ cycloalkyl.

In some embodiments, in the Chemical Formula 1, $Z_1$ is —$CR_g$— or —N—, $Z_2$ is —$CR_h$— or —N—, $Z_3$ is —$CR_i$— or —N—, $Z_4$ is —$CR_j$— or —N—, $Z_5$ is —$CR_k$— or —N—, and only one of $Z_1$ to $Z_5$ is —N—.

In some embodiments, in the Chemical Formula 1, J is —N—, X is —N—; $W_2$ is —$CR_e$—, $Z_1$ is —$CR_g$— or —N—, $Z_2$ is —$CR_h$— or —N—, $Z_3$ is —$CR_i$— or —N—, $Z_4$ is —$CR_j$— or —N—, $Z_5$ is —$CR_k$— or —N—, and only one of $Z_1$ to $Z_5$ is —N—.

In some embodiments, in the Chemical Formula 1, $R_2$ is one selected from the group consisting of substituted or unsubstituted oxazole, substituted or unsubstituted oxacyclobutane containing a chiral central carbon, substituted or unsubstituted imidazole, substituted or unsubstituted $C_1$-$C_4$ alkyl, and substituted or unsubstituted $C_3$-$C_5$ cycloalkyl, where the substituted oxazole, oxacyclobutane, imidazole, alkyl, and cycloalkyl include at least one substitution with —OH, —($C_1$-$C_4$ alkyl), halogen, or —CN.

In some embodiments, in the Chemical Formula 1, $R_2$ is substituted or unsubstituted

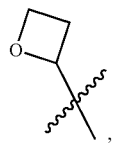

substituted or unsubstituted

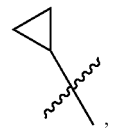

or substituted or unsubstituted

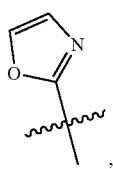 [SMILES: *c1ncco1]

where the substituted

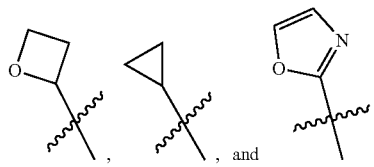

include at least one substitution with —OH, —($C_1$-$C_4$ alkyl), halogen, or —CN.

In some embodiments, in the Chemical Formula 1, Y is —CH—.

In another aspect, the present disclosure provides compounds of the following Chemical Formula 2, optical isomers of the compounds, or pharmaceutically acceptable salts of the compounds or the optical isomers:

[Chemical Formula 2]

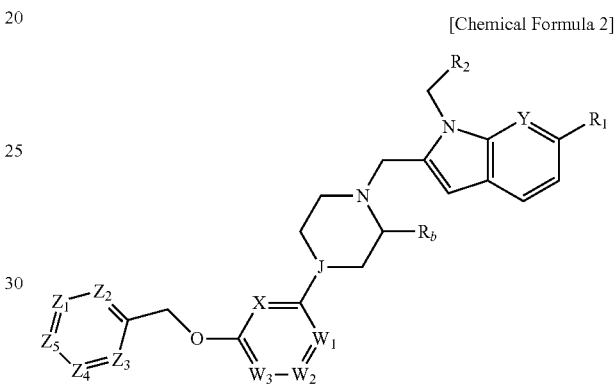

wherein $Z_1$ is —$CR_g$— or —N—, $Z_2$ is —$CR_h$— or —N—, $Z_3$ is —$CR_i$— or —N—, $Z_4$ is —$CR_j$— or —N—, $Z_5$ is —$CR_k$— or —N—, and at least one of $Z_1$ to $Z_5$ is —N— and wherein X, $W_1$, $W_2$, $W_3$, J, $R_b$, $R_2$, Y, and $R_1$ are the same as those defined with regard to the Chemical Formula 1.

In some embodiments, in the Chemical Formula 2, $Z_1$ is —$CR_g$— or —N—, $Z_2$ is —$CR_h$— or —N—, $Z_3$ is —$CR_i$— or —N—, $Z_4$ is —$CR_j$— or —N—, $Z_5$ is —$CR_k$— or —N—, and only one of $Z_1$ to $Z_5$ is —N—.

In another aspect, the present disclosure provides compounds of the following Chemical Formula 3, optical isomers of the compounds, or pharmaceutically acceptable salts of the compounds or the optical isomers:

[Chemical Formula 3]

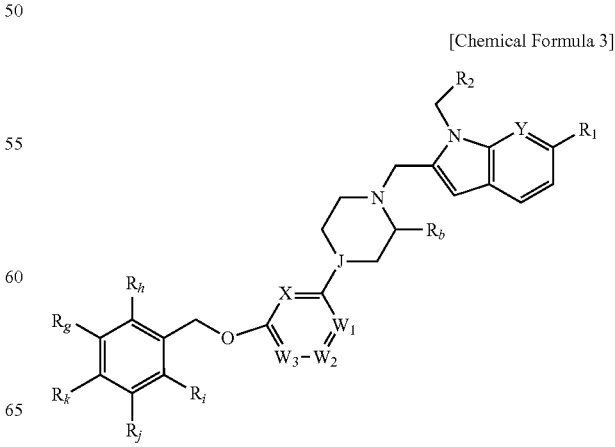

-continued wherein 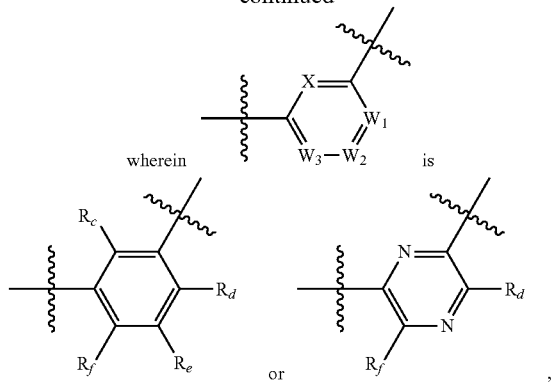 is and wherein $R_g$, $R_h$, $R_i$, $R_j$, $R_k$, X, $W_1$, $W_2$, $W_3$, $R_c$, $R_d$, $R_e$, $R_f$, J, $R_b$, $R_2$, Y, and $R_1$ are the same as those defined with regard to the Chemical Formula 1 above.

In some embodiments, in the Chemical Formula 3, when

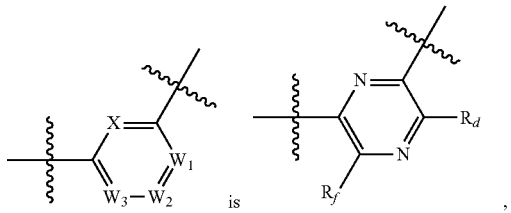

$R_b$ is —($C_1$-$C_4$ alkyl).

In some embodiments, in the Chemical Formula 3, when

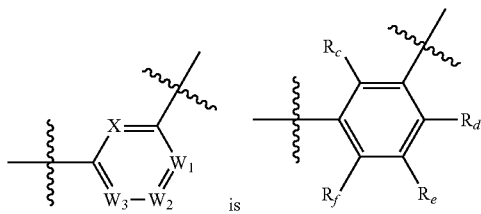

and J is —CH—, Y is —N—.

In some embodiments, in the Chemical Formula 3, when

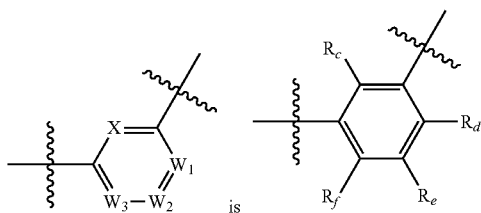

and J is —N—, $R_2$ is substituted or unsubstituted $C_3$ to $C_8$ cycloalkyl.

In still another aspect, the present disclosure provides compounds of the following Chemical Formula 3-1, optical isomers of the compounds, or pharmaceutically acceptable salts of the compounds or the optical isomers:

[Chemical Formula 3-1]

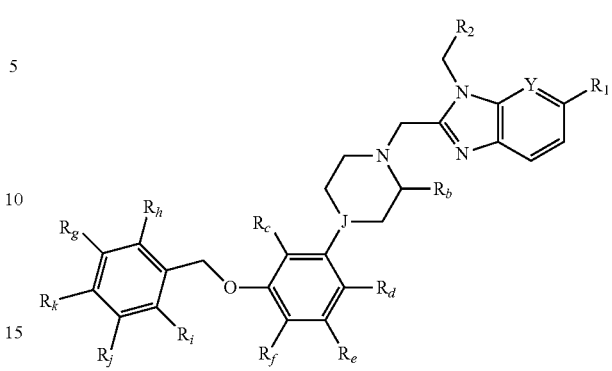

wherein $R_g$, $R_h$, $R_i$, $R_j$, $R_k$, $R_c$, $R_d$, $R_e$, $R_f$, J, $R_b$, $R_2$, Y, and $R_1$ are the same as those defined with regard to the Chemical Formula 1 above.

In yet another aspect, the present disclosure provides compounds of the following Chemical Formula 3-2, optical isomers of the compounds, or pharmaceutically acceptable salts of the compounds or the optical isomers:

[Chemical Formula 3-2]

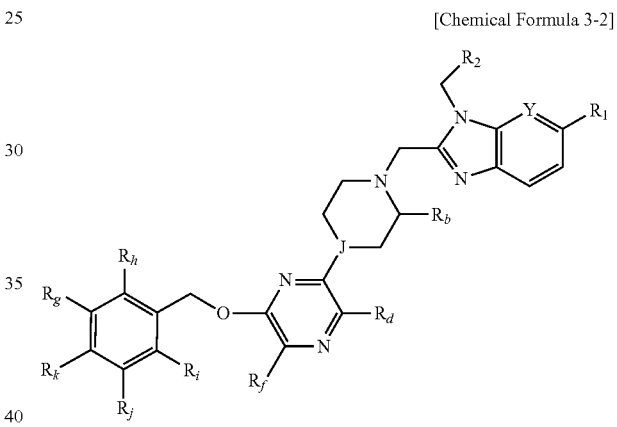

wherein $R_g$, $R_h$, $R_i$, $R_j$, $R_k$, $R_d$, $R_f$, J, $R_b$, $R_2$, Y, and $R_f$ are the same as those defined with regard to the Chemical Formula 1 above.

In yet another aspect, the present disclosure provides compounds represented by the following Chemical Formula 4, optical isomers of the compounds, or pharmaceutically acceptable salts of the compounds or the optical isomers:

[Chemical Formula 4]

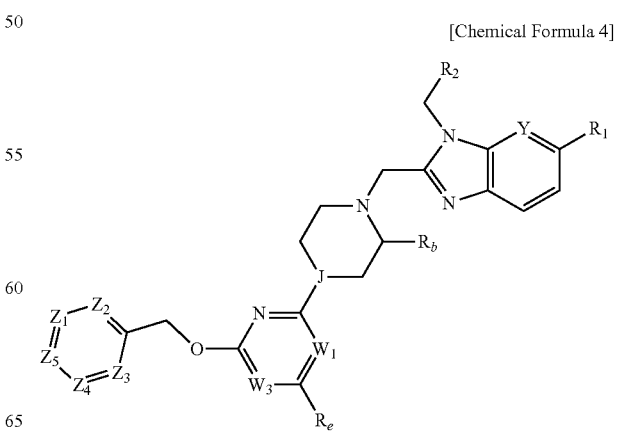

wherein $Z_1$ is —$CR_g$— or —N—; $Z_2$ is —$CR_h$— or —N—; $Z_3$ is —$CR_i$— or —N—; $Z_4$ is —$CR_j$— or —N—; $Z_5$ is —$CR_k$— or —N—; and only one of $Z_i$ to $Z_5$ is —N—, and wherein $W_1$, $R_e$, $W_3$, $R_b$, $R_2$, Y, and $R_1$ are the same as those defined with regard to the Chemical Formula 1 above.

In a further aspect, the present disclosure provides compounds represented by the following Chemical Formula 5, optical isomers of the compounds, or pharmaceutically acceptable salts of the compounds or the optical isomers:

[Chemical Formula 5]

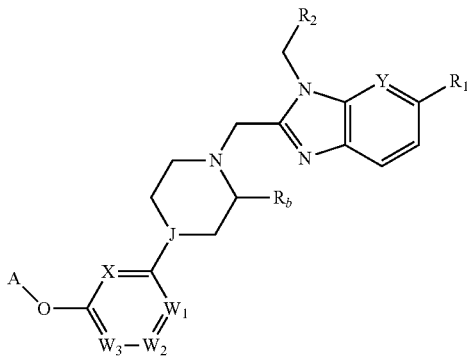

wherein A, X, $W_1$, $W_2$, $W_3$, J, $R_b$, $R_2$, and $R_1$ are the same as those defined with regard to the Chemical Formula 1 above.

In some embodiments, the present disclosure provides the compounds listed below, optical isomers of the compounds, or pharmaceutically acceptable salts of the compounds or the optical isomers:

1-(oxazol-2-ylmethyl)-2-((4-(6-(pyridin-4-ylmethoxy)pyridin-2-yl)piperazin-1-yl)methyl)-1H-benzo[d]imidazole-6-carboxylic acid;

1-(oxazol-2-ylmethyl)-2-((4-(6-(pyridin-2-ylmethoxy)pyridin-2-yl)piperazin-1-yl)methyl)-1H-benzo[d]imidazole-6-carboxylic acid;

(S)-2-((4-(6-((5-chloro-3-fluoropyridin-2-yl)methoxy)pyridin-2-yl)piperazin-1-yl)methyl)-1-(oxetan-2-ylmethyl)-1H-benzo[d]imidazole-6-carboxylic acid;

(S)-2-((4-(6-((5-chloro-3-fluoropyridin-2-yl)methoxy)pyridin-2-yl)piperidin-1-yl)methyl)-1-(oxetan-2-ylmethyl)-1H-benzo[d]imidazole-6-carboxylic acid;

(S)-2-((4-(6-((5-cyanopyridin-2-yl)methoxy)pyridin-2-yl)piperidin-1-yl)methyl)-1-(oxetane-2-ylmethyl)-1H-benzo[d]imidazole-6-carboxylic acid;

1-(oxazol-2-ylmethyl)-2-((4-(6-(pyridin-3-ylmethoxy)pyridin-2-yl)piperazin-1-yl)methyl)-1H-benzo[d]imidazole-6-carboxylic acid;

(S)-2-((4-(6-((5-cyanopyridin-2-yl)methoxy)pyridin-2-yl)piperazin-1-yl)methyl)-1-(oxetane-2-ylmethyl)-1H-benzo[d]imidazole-6-carboxylic acid;

(S)-2-((4-(3-((5-chloro-3-fluoropyridin-2-yl)methoxy)phenyl)piperidin-1-yl)methyl)-1-(oxetane-2-ylmethyl)-1H-benzo[d]imidazole-6-carboxylic acid;

(S)-2-((4-(6-((5-cyanopyridin-2-yl)methoxy)pyrazin-2-yl)piperazin-1-yl)methyl)-1-(oxetane-2-ylmethyl)-1H-benzo[d]imidazole-6-carboxylic acid;

(S)-2-((4-(3-((5-cyanopyridin-2-yl)methoxy)phenyl)piperazin-1-yl)methyl)-1-(oxetan-2-ylmethyl)-1H-benzo[d]imidazole-6-carboxylic acid;

(S)-2-((4-(6-((5-cyanopyridin-2-yl)methoxy)pyridin-2-yl)piperazin-1-yl)methyl)-3-(oxetan-2-ylmethyl)-3H-imidazo[4,5-b]pyridin-5-carboxylic acid;

(S)-2-((4-(3-((5-cyanopyridin-2-yl)methoxy)phenyl)piperazin-1-yl)methyl)-3-(oxetan-2-ylmethyl)-3H-imidazo[4,5-b]pyridine-5-carboxylic acid;

(S)-2-((4-(6-((5-chloropyridin-2-yl)methoxy)pyridin-2-yl)piperazin-1-yl)methyl)-1-(oxetane-2-ylmethyl)-1H-benzo[d]imidazole-6-carboxylic acid;

2-(((S)-4-(6-((5-cyanopyridin-2-yl)methoxy)pyridin-2-yl)-2-methylpiperazin-1-yl)methyl)-1-(((S)-oxetan-2-yl)methyl)-1H-benzo[d]imidazole-6-carboxylic acid;

2-(((S)-4-(6-((5-cyanopyridin-2-yl)methoxy)pyridin-2-yl)-2-methylpiperazin-1-yl)methyl)-3-(((S)-oxetan-2-yl)methyl)-3H-imidazo[4,5-b]pyridin-5-carboxylic acid;

(S)-2-((4-(3-((4-cyano-2-fluorobenzyl)oxy)phenyl)piperidin-1-yl)methyl)-3-(oxetan-2-ylmethyl)-3H-imidazo[4,5-b]pyridine-5-carboxylic acid;

2-((4-(3-((4-cyano-2-fluorobenzyl)oxy)phenyl)piperazin-1-yl)methyl)-1-((1-fluorocyclopropyl)methyl)-1H-benzo[d]imidazole-6-carboxylic acid; and 2-(((S)-4-(6-((4-cyano-2-fluorobenzyl)oxy)pyrazin-2-yl)-2-methylpiperazin-1-yl)methyl)-1-(((S)-oxetan-2-yl)methyl)-1H-benzo[d]imidazole-6-carboxylic acid; an optical isomer thereof or a pharmaceutically acceptable salt thereof.

In yet another aspect, the present disclosure provides pharmaceutical compositions comprising at least one of the compounds of the Chemical Formula 1, 2, 3, 3-1, 3-2, 4 or 5, at least one of optical isomers of the compounds, at least one of pharmaceutically acceptable salts of the compounds or the optical isomers, or any combination thereof.

In a still further aspect, the present disclosure provides pharmaceutical compositions comprising at least one of the compounds of the Chemical Formula 1, 2, 3, 3-1, 3-2, 4 or 5, at least one of optical isomers of the compounds, at least one of pharmaceutically acceptable salts of the compounds or the optical isomers, or any combination thereof, and a pharmaceutically acceptable carrier.

In a still further aspect, the present disclosure provides the compounds of the Chemical Formula 1, 2, 3, 3-1, 3-2, 4 or 5, at least one of optical isomers of the compounds, at least one of pharmaceutically acceptable salts of the compounds or the optical isomers, or any combination thereof for use in treatment and/or prevention of metabolic diseases.

In a still further aspect, the present disclosure provides methods for treating metabolic diseases, the method comprising administering to a subject at least one of the compounds of the Chemical Formula 1, 2, 3, 3-1, 3-2, 4 or 5, at least one of optical isomers of the compounds, at least one of pharmaceutically acceptable salts of the compounds or the optical isomers, or any combination thereof.

In a still further aspect, the present disclosure provides uses of the compounds of the Chemical Formula 1, 2, 3, 3-1, 3-2, 4 or 5, at least one of optical isomers of the compounds, at least one of pharmaceutically acceptable salts of the compounds or the optical isomers, or any combination thereof for prevention or treatment of metabolic diseases.

In a still further aspect, the present disclosure provides uses of the compounds of the Chemical Formula 1, 2, 3, 3-1, 3-2, 4 or 5, at least one of optical isomers of the compounds, at least one of pharmaceutically acceptable salts of the compounds or the optical isomers, or any combination thereof for preparation of a medicament for prevention or treatment of metabolic diseases.

In a still further aspect, the present disclosure provides pharmaceutical compositions for prevention or treatment of metabolic diseases comprising at least one of the compounds of the Chemical Formula 1, 2, 3, 3-1, 3-2, 4 or 5, at least one of optical isomers of the compounds, at least one of pharmaceutically acceptable salts of the compounds or the optical isomers, or any combination thereof.

In a still further aspect, the present disclosure provides GLP-1R agonists comprising at least one of the compounds of the Chemical Formula 1, 2, 3, 3-1, 3-2, 4 or 5, at least one of optical isomers of the compounds, at least one of pharmaceutically acceptable salts of the compounds or the optical isomers, or any combination thereof.

The compounds, the optical isomers, and the pharmaceutically acceptable salts of the present disclosure exhibit excellent effects as GLP-1 agonists. Specifically, a result of performing a competitive immunoassay between an intrinsic cAMP generated in a cell and a foreign cAMP labeled with a dye shows that the compounds, optical isomers, and pharmaceutically acceptable salts of the present disclosure have excellent effects as GLP-1 agonists. In addition, a glucose tolerance test on monkeys shows that the compounds, optical isomers, and pharmaceutically acceptable salts of the present disclosure have excellent glucose tolerance in both intravenous and oral administrations as well as have excellent pharmacokinetic properties.

In addition, the compounds, the optical isomers, and the pharmaceutically acceptable salts of the present disclosure exhibit excellent pharmacological safety for cardiovascular systems. Specifically, a result of analysis through an hERG assay shows that the compounds, optical isomers, and pharmaceutically acceptable salts of the present disclosure have significantly high cardiovascular safety and significantly low risk of the cardiac toxicity such as arrhythmia for a long period of administration. Thus, the effect of the compounds, the optical isomers, and the pharmaceutically acceptable salts of the present disclosure is different from or superior to that of existing compound.

The term metabolic disease used herein includes, for example, diabetes (T1D and/or T2DM, such as prediabetes), idiopathic T1D (type 1b), latent autoimmune diabetes in adults (LADA), early onset T2DM (EOD), younger onset atypical diabetes (YOAD), maturity onset diabetes in young (MODY), malnutrition-related diabetes, gestational diabetes, hyperglycemia, insulin resistance, liver insulin resistance, impaired glucose tolerance, diabetic neuropathy, diabetic nephropathy, kidney disease (e.g., acute kidney failure, tubular dysfunction, pro-inflammatory changes to proximal tubule), diabetic retinopathy, adipocyte dysfunction, visceral fat accumulation, sleep apnea, obesity (e.g., hypothalamic obesity and monogenic obesity) and associated comorbidities (e.g. osteoarthritis and urinary incontinence), eating disorders (e.g., binge eating syndrome, anorexia nervosa, and syndrome of obesity, such as Prader-Willi syndrome and Barde-Biedl syndrome), weight gain due to use of other drugs (e.g. from use of steroids and antipsychotics), excessive sugar intake, dyslipidemia (including hyperlipidemia, hypertriglyceridemia, increased total cholesterol, high LDL cholesterol, and low HDL cholesterol), hyperinsulinemia, NAFLD (including related diseases such as steatosis, NASH, fibrosis, cirrhosis, and hepatocellular carcinoma), cardiovascular disease, atherosclerosis (including coronary artery disease), peripheral vascular disease, hypertension, endothelial dysfunction, impaired vascular compliance, congestive heart failure, myocardial infarction (e.g., necrosis and apoptosis), stroke, hemorrhagic stroke, ischemic stroke, traumatic brain injury, pulmonary hypertension, restenosis after angioplasty, intermittent claudication, postprandial lipidemia, metabolic acidosis, ketosis, arthritis, osteoporosis, Parkinson's disease, left ventricular hypertrophy, peripheral arterial disease, loss of vision, cataracts, glomerulosclerosis, chronic renal failure, metabolic syndrome, X syndrome, premenstrual syndrome, angina, thrombosis, atherosclerosis, transient ischemic attack, vascular restenosis, impaired glucose metabolism, symptoms of impaired fasting blood sugar, hyperuricemia, gout, erectile dysfunction, skin and connective tissue disorders, psoriasis, foot ulcers, ulcerative colitis, hyper-apo B lipoproteinemia, Alzheimer's disease, schizophrenia, cognitive impairment, inflammatory bowel disease, short bowel syndrome, Crohn's disease, colitis, irritable bowel syndrome, polycystic ovary syndrome, and addiction (e.g., alcohol and/or drug abuse).

As used herein, the term "alkyl" refers to a straight or branched chain monovalent hydrocarbon group of a structural formula —$C_nH_{(2n+1)}$. Non-limiting examples thereof include methyl, ethyl, propyl, isopropyl, butyl, 2-methyl-propyl, 1,1-dimethylethyl, pentyl and hexyl, and the like. For example, "$C_1$-$C_4$ alkyl" may refer to alkyl such as methyl, ethyl, propyl, butyl, 2-methyl-propyl, or isopropyl.

As used herein, the term "$C_6$-$C_{12}$ aryl" refers to an aromatic hydrocarbon containing 6 or 12 carbon atoms. The term "$C_6$-$C_{12}$ aryl" refers to, for example, a ring system such as monocyclic (e.g., phenyl) or bicyclic (e.g., indenyl, naphthalenyl, tetrahydronaphthyl, tetrahydroindenyl).

As used herein, the term "$C_5$-$C_{12}$ heteroaryl" refers to an aromatic hydrocarbon containing 5 to 12 carbon atoms in which at least one of ring carbon atoms is replaced with a heteroatom selected from oxygen, nitrogen and sulfur. The heteroaryl group may be attached via a ring carbon atom or, if valency permits, via a ring nitrogen atom or the like. The heteroaryl group includes a benzo condensed ring system having 2 to 3 rings.

As used herein, the term "$C_3$-$C_8$ cycloalkyl" refers to a cyclic monovalent hydrocarbon group of a structural formula —$C_nH_{(2n-1)}$ containing 3 to 8 carbon atoms. Non-limiting examples thereof include cyclopropyl, cyclobutyl, cyclopentyl, cyclohexyl, cycloheptyl, and cyclooctyl.

As used herein, the term "$C_3$-$C_8$ heterocycloalkyl" refers to a cycloalkyl group containing 3 to 8 carbon atoms in which at least one of ring methylene groups (—$CH_2$—) is replaced with a group selected from —O—, —S— and nitrogen. In this case, nitrogen may provide an attachment point or may be substituted based on embodiments.

As used herein, the term "unsubstituted" means a state that hydrogen is not substituted with any substituent.

As used herein, the term "substituted aryl, heteroaryl, heterocycloalkyl and cycloalkyl" may include at least one substitution, that is, 1, 2, 3, 4, 5, 6 or more substitutions with —OH, —($C_1$-$C_4$ alkyl), halogen, or —CN. Each of these substitutions may be made independently.

As used herein, the term "halogen" refers to fluoride, chloride, bromide, or iodide.

As used herein, the term "haloalkyl" refers to an alkyl group in which hydrogen is substituted with one or more halogens (e.g., fluoride, chloride, bromide, or iodide).

Following abbreviations in the present disclosure represent following corresponding terms:

EA: ethyl acetate
MC: methyl chloride
BINAP: 2,2'-bis(diphenylphosphino)-1,1'-binapthyl
DCM: dichloromethane
MTBE: methyl tert-butyl ether
MPLC: medium pressure liquid chromatography
TEA: triethylamine
DMF: dimethylformamide
THF: tetrahydrofuran
p-TSA: para-toluenesulfonic acid
TBD: triazabicyclodecene
PTLC: Prepared thin layer chromatography DMSO: dimethyl sulfoxide
Pd$_2$(dba)$_3$: tris(dibenzylideneacetone)dipalladium(0)
MeOH: methanol
KOtBu: potassium tert-butoxide
ADDP: 1,1'-(azodicarbonyl)dipiperidine
A wavy line

herein indicates a point of attachment of a substituent to another group.

In some embodiments, in the Chemical Formula 1, R$_1$ is —C(=O)R$_a$, and R$_a$ is —OH or —O—(C$_1$-C$_4$ alkyl). Preferably, R$_1$ may be —C(=O)OH.

In the Chemical Formula 1, R$_2$ is one selected from the group consisting of substituted or unsubstituted C$_6$ to C$_{12}$ aryl, substituted or unsubstituted C$_5$ to C$_{12}$ heteroaryl, substituted or unsubstituted C$_3$ to C$_8$ heterocycloalkyl, substituted or unsubstituted C$_1$ to C$_4$ alkyl, and substituted or unsubstituted C$_3$ to C$_8$ cycloalkyl, where the substituted aryl, heteroaryl, heterocycloalkyl, alkyl, and cycloalkyl include at least one substitution with —OH, —(C$_1$-C$_4$ alkyl), halogen, or —CN. Preferably, R$_2$ may be one selected from the group consisting of substituted or unsubstituted oxazole, substituted or unsubstituted oxacyclobutane containing a chiral central carbon, substituted or unsubstituted imidazole, substituted or unsubstituted C$_1$-C$_4$ alkyl, and substituted or unsubstituted C$_3$-C$_5$ cycloalkyl, where the substituted oxazole, oxacyclobutane, imidazole, alkyl, and cycloalkyl include at least one substitution with —OH, —(C$_1$-C$_4$ alkyl), halogen, or —CN.

More specifically, R$_2$ may be substituted or unsubstituted

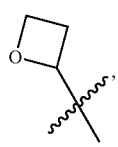 [SMILES: *C1CCO1]

substituted or unsubstituted

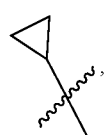 [SMILES: *C1CC1]

or substituted or unsubstituted

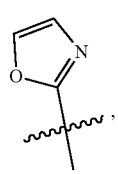 [SMILES: *c1ncco1]

where the substituted

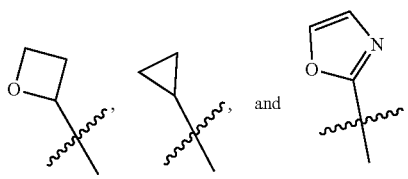

include at least one substitution with —OH, —(C$_1$-C$_4$ alkyl), halogen, or —CN.

In some embodiments, Y may be —CH—.

In some embodiments, in the Chemical Formula 1, when A is a substituted or unsubstituted pyridine,

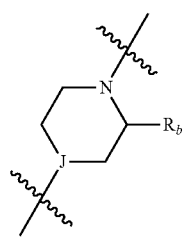

may be one selected from the group consisting of following compounds:

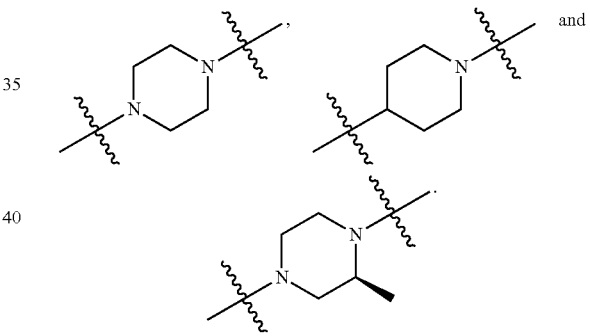

In some embodiments, A is substituted or unsubstituted phenyl or substituted or unsubstituted pyridine, where the substitution may include at least one substitution with one selected from the group consisting of halogen, —CN, —OH, —O—(C$_1$-C$_4$ alkyl), —NH$_2$, —NO$_2$, and —C$_1$-C$_4$haloalkyl.

In some embodiments, when A is phenyl, A may be substituted phenyl, wherein the substitution is one or more substitutions with halogen and/or —CN.

In some embodiments, when A is pyridine, A may be a substituted or unsubstituted pyridine, wherein the substitution is one or more substitutions with halogen and/or —CN.

In some embodiments, A may be one selected from the group consisting of following compounds:

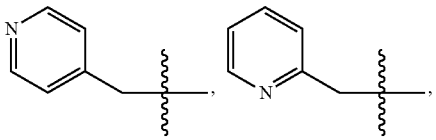

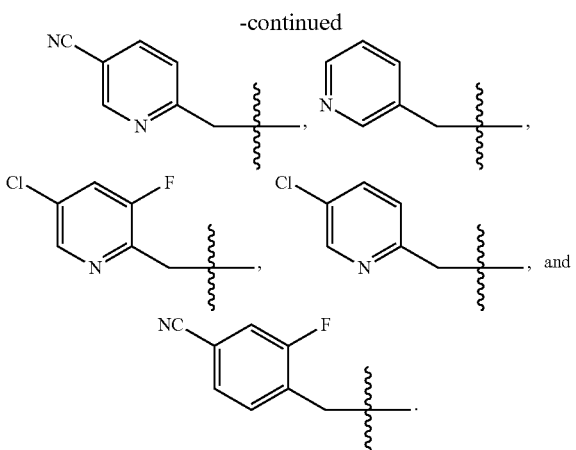

In some embodiments, when A is a substituted or unsubstituted pyridine,

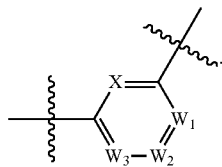

may be one selected from the group consisting of following compounds:

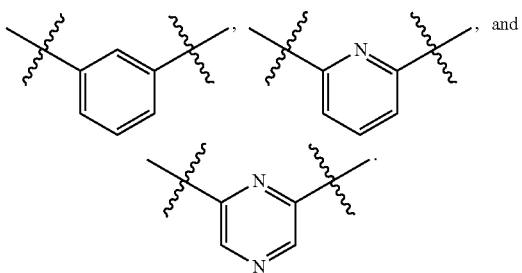

Compounds and intermediates as described below were named using the naming convention provided from ChemBioDraw Ultra. The naming convention is generally consistent with the International Union for Pure and Applied Chemistry (IUPAC) recommendations for nomenclature of organic chemistry and the CAS index rules. It will be appreciated that chemical names may have only parentheses, or both parentheses and brackets. A stereochemical description may be placed at different locations within a name itself, depending on the naming convention. Those of skill in the art will be aware of such formatting variations and may appreciate that they provide the same chemical structure.

The compounds, the optical isomers of the compounds, or pharmaceutically acceptable salts of the compounds or the optical isomers of the present disclosure may comprise acid addition salts and base addition salts.

Suitable acid addition salts are formed from acids that form non-toxic salts. Examples thereof may include acetate, adipate, aspartate, benzoate, besylate, bicarbonate/carbonate, bisulfate/sulfate, borate, camsylate, citrate, cyclamate, ediselate, esylate, formate, fumarate, gluceptate, gluconate, glucuronate, hexafluorophosphate, hybenzate, hydrochloride/chloride, hydrobromide/bromide, hydroiodide/iodide, isethionate, lactate, malate, malcate, malonate, mesylate, methyl sulfate, naphthylate, naphthsylate, 2-naphsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate, 1,5-naphthalenedisulfonic acid, and xinafoate salts.

Suitable base addition salts are formed from bases forming non-toxic salts. Examples thereof may include aluminum, arginine, benzathine, calcium, choline, diethylamine, bis(2-hydroxyethyl)amine (diolamine), glycine, lysine, magnesium, meglumine, 2-aminoethanol (olamine), potassium, sodium, 2-amino-2-(hydroxymethyl) propane-1,3-diol (tris or trimethamine), and zinc salts.

In addition, hemi salts of acids and bases such as hemisulfate and hemicalcium salts may be formed.

The compounds, the optical isomers of the compounds, or pharmaceutically acceptable salts of the compounds or the optical isomers of the present disclosure may exist in unsolvated and solvated forms. As used herein, the term 'solvate' refers to a molecular complex comprising one or more pharmaceutically acceptable solvent molecules (e.g., ethanol) as well as a compound of the Chemical Formula 1, an optical isomer of the compound, or a pharmaceutically acceptable salt of the compound or the optical isomer. The term 'hydrate' refers to a solvate when the solvent is water.

A multi-component complex (in addition to salts and solvates) is also included within the scope of the present disclosure. In this connection, a medicament and one or more other components are then present in a stoichiometric or non-stoichiometric amount. The complex of this type includes inclusion compounds (drug-host inclusion complexes) and co-crystals. Co-crystals are typically defined as crystalline complexes of neutral molecular components that are bonded to each other via non-covalent interactions, but co-crystals may be complexes of neutral molecules with salts. Co-crystals may be prepared by melt crystallization, by recrystallization from a solvent, or by physically grinding the components together.

The compounds, the optical isomers of the compounds, or pharmaceutically acceptable salts of the compounds or the optical isomers of the present disclosure may exist as a solid state continuum ranging from completely amorphous to fully crystalline. The term 'amorphous' refers to a state in which a substance loses a long-distance arrangement regularity at a molecular level and the physical properties of a solid or liquid may be exhibited depending on temperature. Typically, the substance does not provide a unique X-ray diffraction pattern, and exhibits properties of a solid, and is more formally described as a liquid. Upon heating thereof, a change thereof from solid to liquid properties thereof occurs. The substance is characterized by a state change (typically secondary) ('glass transition'). The term 'crystalline' refers to a solid phase in which a substance has arrangement regularity at the molecular level and provides an X-ray diffraction pattern with defined peaks. The substance will also exhibit the properties of a liquid when heated sufficiently, but the change thereof from solid to liquid is characterized by a phase change (typically primary) ('melting point').

The compounds of the present disclosure that contain one or more asymmetric carbon atoms may exist as two or more stereoisomers. When structural isomers are convertible to each other through a low energy barrier, tautomeric isomerism or tautomerism may occur. This may, for example, take a form of proton tautomerism in the compound of the Chemical Formula 1 containing imino, keto, or oxime groups, or take a form of valence tautomerism in the compound thereof containing aromatic residues. As a result, a single compound may exhibit at least two types of isomerism.

The pharmaceutically acceptable salts of the compounds of the present disclosure may contain counter-ions that are optically active or racemic.

Conventional techniques for the preparation/isolation of individual enantiomers include chiral synthesis from suitable optically pure precursors, for example, resolution of racemic bodies (or racemic bodies of salts or derivatives) using chiral high pressure liquid chromatography (HPLC). Alternatively, the racemic body (or racemic precursor) may react with base or acid (e.g. 1-phenylethylamine or tartaric acid), when a suitable optically active compound, e.g., an alcohol, or the compound of the Chemical Formula 1 contains acidic or basic residues. The resulting diastereomeric mixture may be separated using chromatography and/or fractional crystallization, and one or both of the diastereomers may be converted to the corresponding pure enantiomer(s) using means well known to those skilled in the art. A chiral compound of the Chemical Formula 1 (and a chiral precursor thereof) may be obtained in an enantiomer-enriched form using chromatography, typically HPLC, on asymmetric resins using a mobile phase composed of hydrocarbons, typically heptane or hexane, containing 0 to 50% by volume, typically 2% to 20% by volume of isopropanol, and 0 to 5% by volume of alkylamine, typically 0.1% by volume of diethylamine. Concentration of the eluent results in an enriched mixture. Chiral chromatography using subcritical and supercritical fluids may be used. Chiral chromatography methods useful in some embodiments of the present disclosure are known in the art.

When any racemic body crystallizes, two different types of crystals are possible. A first type is the above mentioned racemic compound (intrinsic racemic body) in which crystal of one homogeneous form containing both enantiomers in an equimolar amount is formed. A second type is a racemic mixture or conglomerate in which crystals of two forms, each comprising a single enantiomer, are produced in an equimolar amount. Although both the crystal forms present in the racemic mixture have the same physical properties, they may have different physical properties from those of the true racemic body. The racemic mixture may be separated using conventional techniques known to those skilled in the art.

The compounds, the optical isomers of the compounds, or pharmaceutically acceptable salts of the compounds or the optical isomers of the present disclosure may exist as a prodrug thereof.

Administration and Dosage

Typically, the compounds, the optical isomers of the compounds, or pharmaceutically acceptable salts of the compounds or the optical isomers of the present disclosure may be administered in an amount effective to treat the symptoms described herein. For administration and dosage purposes, the compounds, the optical isomers, or the pharmaceutically acceptable salts of the present disclosure may, for the sake of simplicity, be referred to as the compound or compounds according to the present disclosure.

The compound according to the present disclosure is administered via any suitable route, in a form of a pharmaceutical composition suitable for the route, and in a dosage effective for intended treatment. The compound according to the present disclosure may be administered orally, or in rectal, vaginal, parenteral, or topical manner.

The compound according to the present disclosure may preferably be administered orally. Oral administration may involve swallowing to allow the compound to enter the gastrointestinal tract, or it may include buccal or sublingual administration to allow the compound to enter the bloodstream directly from the oral cavity.

In some embodiments, the compound according to the present disclosure may be administered directly to the bloodstream, muscle or internal organs. Suitable means for parenteral administration include intravenous, intraarterial, intraperitoneal, intrathecal, intraventricular, intraurethral, intrasternal, intracranial, intramuscular and subcutaneous administration. Devices suitable for parenteral administration include needle (including microneedle) syringes, needleless syringes and infusion techniques.

In other embodiments, the compound according to the present disclosure may be administered topically (that is, in epidermal or transdermal manner) to the skin or mucous membrane. In still another embodiment, the compound according to the present disclosure may be administered intranasally or by inhalation. In still other embodiments, the compound according to the present disclosure may be administered rectally or intravaginally. In yet other embodiments, the compound according to the present disclosure may be administered directly to the eye or ear.

The compound according to the present disclosure and/or the composition containing the compound may be administered based on various factors including a type, age, weight, sex and medical symptom of the patient; severity of symptoms; route of administration; and activity of a particular compound as used. Thus, the administration scheme may vary widely. In some embodiments, a total daily dose of the compound according to the present disclosure may be typically about 0.001 to about 100 mg/kg (i.e., mg of the compound according to the present disclosure per kg body weight) for the treatment of the symptoms discussed herein. In other embodiments, the total daily dose of the compound according to the present disclosure may be about 0.01 to about 30 mg/kg, about 0.03 to about 10 mg/kg, or about 0.1 to about 3 mg/kg. It is not unusual for the administration of the compound according to the present disclosure to be repeated several times a day (typically no more than 4 times a day). The multiple doses per day may typically be used to increase the total daily dose, if necessary.

In the oral administration, the composition may be provided in the form of tablets, capsules, liquids, etc. for symptom-related control of the dosage to the patient. The medicament typically contains from about 0.01 mg to about 500 mg of the active ingredient.

Suitable subjects according to the present disclosure include mammalians. In some embodiments, humans are suitable subjects. Human subjects may be male or female and may be at any stage of growth.

Pharmaceutical Compositions

In one aspect, the present disclosure provides pharmaceutical compositions. More specifically, some embodiments of the present disclosure provide pharmaceutical compositions for preventing and treating metabolic diseases, the compositions each comprising at least one of the compounds represented by Chemical Formula 1, at least one of optical isomers of the compounds, at least one of pharmaceutically acceptable salts of the compounds or the optical isomers, or any combination thereof. The pharmaceutical compositions each may further comprise at least one of pharmaceutically acceptable carriers. As used herein, the term "pharmaceutically acceptable carrier" includes any and all of physiologically compatible solvents, dispersion media, coatings, antibacterial and antifungal agents, isotonic and absorption delaying agents, and the like. Examples of the pharmaceutically acceptable carriers include one or more of water, saline, phosphate buffered saline, dextrose, glycerol, ethanol, as well as combinations thereof. Isotonic agents such as sugar, sodium chloride, or polyalcohols such as mannitol or sorbitol may be contained in the composition.

The pharmaceutical compositions each may further comprise at least one of pharmacologically active ingredients. For example, a pharmaceutically acceptable ingredient (e.g., wetting agent) or a small amount of an auxiliary ingredient (e.g., wetting agent, emulsifying agent, preservative, or buffer) that can enhance the shelf life or effectiveness of an antibody or a portion thereof may be contained in the composition.

The composition according to the present disclosure may be in various forms. The composition according to the present disclosure may be in a form of, for example, liquid, semi-solid and solid dosage, such as liquid solutions (e.g., injectable and injectable solutions), dispersions or suspensions, tablets, pills, powders, liposomes and suppositories. The form depends on the intended route of administration and therapeutic purpose thereof.

A typical composition is in the form of injectable and infusible solutions. One mode of administration is a parenteral mode (e.g., intravenous, subcutaneous, intraperitoneal, intramuscular mode). In some embodiments, a drug may be administered via intravenous infusion or injection. In some other embodiments, a drug may be administered via intramuscular or subcutaneous injection.

Oral administration of a solid formulation may be achieved, for example, based on hard or soft capsules, pills, cachets, lozenges or tablets, each containing a predetermined amount of one or more compounds according to the present disclosure. In some embodiments, oral administration may be achieved based on powder or granular form. In some other embodiments, the oral dosage form may be sublingual form, for example, lozenge. In the solid dosage form, the compound of the Chemical Formula 1 is usually combined with one or more excipients. The capsules or tablets may contain controlled release formulations. The capsules, tablets and pills may also contain a buffering agent or may be prepared into an enteric coating.

In still other embodiments, oral administration may be achieved in a liquid dosage form. The liquid dosage forms for oral administration include, for example, pharmaceutically acceptable emulsions, solutions, suspensions, syrups, and elixirs containing inert diluents (e.g., water) commonly used in the art. The composition may contain excipients such as wetting agents, emulsifying agents, suspending agents, flavoring agents (e.g., sweetening agents), and/or fragrances.

In some embodiments, the present disclosure provides parenteral dosage forms of the composition. As used herein, the term "parenteral administration" includes, for example, subcutaneous injection, intravenous injection, intraperitoneal injection, intramuscular injection, intrasternal injection, and infusion. Injectable preparations (i.e., sterile injectable aqueous or oleaginous suspensions) may be formulated according to known techniques using suitable dispersing, wetting and/or suspending agents.

Other carrier substances and modes of administration known in the pharmaceutical art may be used. The pharmaceutical composition according to the present disclosure may be prepared by any well-known pharmaceutical technique, such as effective formulation and administration procedures. The considerations related to the effective formulation and administration procedures are well known in the art, and they are described in standard textbooks.

Kits

In another aspect, the present disclosure provides kits each containing at least one of the compounds of the present disclosure, at least one of the optical isomers of the compounds, at least one of the pharmaceutically acceptable salts of the compounds or the optical isomers, or any combination thereof. In some embodiments, the present disclosure provides kits each containing a composition that comprises at least one of the compounds, at least one of the optical isomers of the compounds, at least one of the pharmaceutically acceptable salts of the compounds or the optical isomers, or any combination thereof.

An exemplary kit may contain a diagnostic agent or a therapeutic agent in addition to the compound, the optical isomer, the pharmaceutically acceptable salt, or the composition. The kit includes instructions for use in a diagnostic or therapeutic method. In some embodiments, the kit comprises the compound of the Chemical Formula 1, 2, 3, 3-1, 3-2, 4, or 5, or the pharmaceutical composition containing the compound, and a diagnostic agent. In some other embodiments, the kit comprises the compound of the Chemical Formula 1, 2, 3, 3-1, 3-2, 4, or 5, or the pharmaceutical composition containing the compound.

In still other embodiments, the present disclosure provides kits each suitable for use in carrying out the treatment methods described herein. In some embodiments, the kit contains a first dosage formulation comprising one or more compounds according to the present disclosure in an amount sufficient to carry out the method according to the present disclosure. In some other embodiments, the kit contains one or more compounds according to the present disclosure in an amount sufficient to carry out the method according to the present disclosure, and a container for administration thereof.

Preparation

Reaction Formulas as described below are intended to provide a general description of the methodology used in the preparation of the compounds, optical isomers, or pharmaceutical acceptable salts according to the present disclosure. Some of the compounds according to the present disclosure may contain single or multiple chiral centers with stereochemical designations (R) or (S). It will be apparent to those skilled in the art that whether the substance is enantiomer-enriched or is a racemic body, all synthetic conversions may be carried out in a similar manner.

In addition, separation of an optically active target substance may be carried out at any desired point in a sequence using known methods as described herein and in the chemical literature.

In following Reaction formulas, the variables X, Y, $W_1$, $W_2$, $W_3$, $Z_1$, $Z_2$, $Z_3$, $Z_4$, $Z_5$, J, $R_1$, $R_2$, $R_a$, $R_b$, $R_c$, $R_d$, $R_e$, $R_f$, $R_g$, $R_h$, $R_i$, $R_j$, and $R_k$ are the same as described herein with reference to the compound of the Chemical Formula 1, 2, 3, 3-1, 3-2, 4, or 5, unless otherwise stated.

The compounds of the Chemical Formula 1, 2, 3, 3-1, 3-2, 4, or 5 according to the present disclosure include compounds of the following Examples as prepared below. The compounds of the Examples may be prepared or provided based on various methods described in the literature and common technical knowledge known to those skilled in the art based on two or more selected from following intermediate compounds. The intermediate compounds may be prepared or provided based on various methods described in the literature and common technical knowledge known to those skilled in the art, in addition to following descriptions.

Methods of preparing the intermediates used to prepare the compounds of the Chemical Formula 1, 2, 3, 3-1, 3-2, 4, or 5 are described in the Preparation Methods 1 to 6 to be described below.

ADVANTAGEOUS EFFECTS

The novel compounds according to the present disclosure exhibit excellent activity as GLP-1 receptor agonists. In particular, the compounds according to the present disclosure, as GLP-1 receptor agonists, exhibit excellent glucose tolerance, thus exhibiting a remarkable effect as a therapeutic agent for metabolic diseases. Moreover, the novel compounds according to the present disclosure exhibit excellent pharmacological safety for cardiovascular systems.

MODE FOR INVENTION

Hereinafter, preferred examples are set forth to aid in understanding the present disclosure. However, the following examples are provided for easier understanding of the present disclosure, and the present disclosure is not limited thereto.

Reagents and solvents as mentioned below were purchased from Sigma-Aldrich, TCI, etc., unless otherwise noted. Waters Alliance high-performance liquid chromatography (HPLC) system was used. Biotage Flash purification system was used as a silica gel used for column chromatography. $^1$H NMR spectra was recorded using Bruker 400 MHz Ascend™ system. Waters Masslynx mass spectrum system was used.

All of $^1$H nuclear magnetic resonance (NMR) spectra were consistent with the chemical structures of the compounds of the Examples of the present invention.

Characteristic chemical shifts (d) are given in parts-per-million (ppm) relative to the residual proton signal in the deuterated solvent (CDCl$_3$: 7.27 ppm; CD$_3$OD: 3.31 ppm; DMSO-d$_6$: 2.50 ppm) and are reported using conventional abbreviations for designation of major peaks: for example, s: singlet; d: doublet; t: triplet; q: quartet; m: multiplet; and br: broad.

SYNTHESIS EXAMPLES

Synthesis Example 1: Synthesis of Intermediates 1 to 19

Exemplary methods of preparing intermediates 1 to 19 are described in detail below. Using the Preparation Methods 1 to 6 described below, those skilled in the art may prepare the compounds listed as intermediates 1 to 19 from appropriate starting materials which are available commercially or may be prepared by methods known in the art.

1. Preparation Method 1

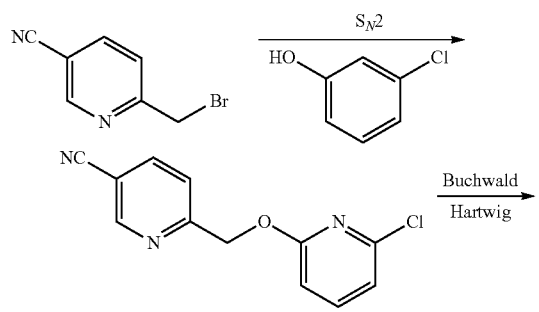

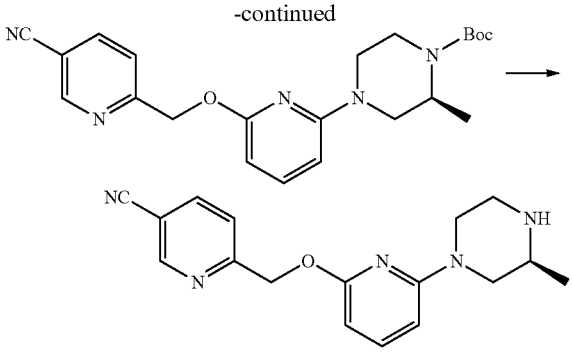

(1) Synthesis of Intermediate 1: (S)-6-(((6-(3-methylpiperazin-1-yl)pyridin-2-yl)oxy)methyl)nicotinonitrile 1) Synthesis of 6-(((6-chloropyridin-2-yl)oxy)methyl)nicotinonitrile 6-bromomethyl-nicotinonitrile (1.52 g) and 6-chloro-2-hydroxypyridine (1.0 g) were placed in a round bottom flask and stirred in toluene (50 mL). Ag$_2$CO$_3$ (4.26 g) was added, and the mixture was heated to 100° C. and stirred for 1 d. After it was confirmed by TLC that the reaction was completed, the mixture was diluted with ethyl acetate (EA) and filtered through a celite pad, and concentrated under reduced pressure. The residue was purified by silica gel column chromatography with hexane/ethyl acetate to obtain the target compound (1.55 g, 82%) as a white solid. LC-MS (ES$^+$): 246 (M+H)$^+$ 2) Synthesis of tert-butyl(S)-4-(6-((5-cyanopyridin-2-yl)methoxy)pyridin-2-yl)-2-methylpiperazine-1-carboxylate The compound (600 mg) synthesized in the step 1), tert-butyl (S)-2-methylpiperazine-1-carboxylate (539 mg), Pd$_2$(dba)$_3$ (112 mg), Cs$_2$CO$_3$ (1.6 g), and BINAP (152 mg) were placed in a round bottom flask and stirred in toluene (20 mL). The mixture was heated to 120° C. under N$_2$ and stirred for 1 d. After it was confirmed by TLC that the reaction was completed, the mixture was diluted with EA, filtered with a celite pad, and concentrated under reduced pressure. The residue was subjected to silica gel column chromatography with hexane/ethyl acetate eluent system to obtain the target compound (603 mg, 60%) as a syrup LC-MS(ES$^+$): 410 (M+H)$^+$ 3) Synthesis of (S)-6-(((6-(3-methylpiperazin-1-yl)pyridin-2-yl)oxy)methyl)nicotinonitrile The compound (603 mg) synthesized in the step 2) was placed in a round bottom flask, dissolved in DCM (10 mL), and stirred. While the mixture was stirred, TFA (1.5 mL) was dropwise added to the mixture at 0° C. The resulting mixture was then stirred at room temperature for 6 h. After it was confirmed by TLC that the reaction was completed, the mixture was neutralized with sat. aqueous NaHCO$_3$ solution, extracted with DCM/MeOH 10% solution, dried over anhydrous magnesium sulfate, filtered under reduced pressure, and concentrated under reduced pressure to give the target compound (512 mg) as a brown solid. LC-MS(ES$^+$): 310 (M+H)$^+$

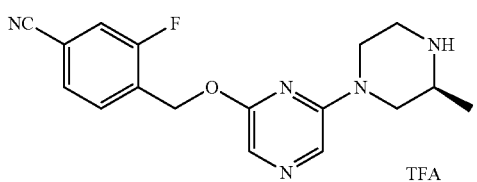 [SMILES: C[C@H]1CN(c2cncc(OCc3ccc(C#N)cc3F)n2)CCN1]

(2) Synthesis of Intermediate 2: (S)-3-fluoro-4-(((6-(3-methylpiperazin-1-yl)pyrazin-2-yl)oxy)methyl)benzonitrile trifluoroaceticacid salt The intermediate 2 was synthesized according to the Preparation Method 1.

1) Synthesis of 4-(((6-chloropyrazin-2-yl)oxy)methyl)-3-fluorobenzonitrile 6-chloropyrazine-2-ol (1 eq.) and 4-(bromomethyl)-3-fluorobenzonitrile (1 eq.) were placed in a round bottom flask and stirred in $CH_3CN$ (0.1 M). After $K_2CO_3$ (3 eq.) was added, the resulting mixture was stirred at room temperature for 2 h. After it was confirmed by TLC that the reaction was completed, the mixture was diluted with water and extracted with EA. The resulting organic layer was washed with brine solution, dried over anhydrous magnesium sulfate, and filtered under reduced pressure to obtain a filtrate. The filtrate was concentrated under reduced pressure. The residue was purified by silica gel column chromatography with a hexane/ethyl acetate to obtain the target compound (82%) as a white solid. LC-MS(ES+): 264 (M+H)+

2) Synthesis of tert-butyl (S)-4-(6-((4-cyano-2-fluorobenzyl)oxy)pyrazin-2-yl)-2-methylpiperazine-1-carboxylate The compound (1 eq.) synthesized in the step 1), tert-butyl (S)-2-methylpiperazine-1-carboxylate (1.1 eq.), $Cs_2CO_3$ (2 eq.), BINAP (0.1 eq.), and $Pd_2(dba)_3$ (0.05 eq.) were placed in a round bottom flask and stirred in toluene (0.2 M). The mixture was heated to 120° C. under nitrogen and stirred for 16 h. After it was confirmed by TLC that the reaction was completed, the reaction mixture was diluted with EA and filtered through a celite pad. Water was added to the filtrate, and the filtrate was extracted with EA. The resulting organic layer was washed with brine solution, dried over anhydrous magnesium sulfate, and filtered under reduced pressure to obtain a filtrate. The filtrate was concentrated under reduced pressure. The residue was purified by silica gel column chromatography with hexane/ethyl acetate to obtain the target compound (73%) as a white solid. LC-MS(ES+): 428 (M+H)+

3) Synthesis of (S)-3-fluoro-4-(((6-(3-methylpiperazin-1-yl)pyrazin-2-yl)oxy)methyl)benzonitrile The compound (710 mg) synthesized in the step 2) was placed in a round bottom flask and stirred in DCM (2 mL). While the mixture was stirred, TFA (1.68 mL) was added dropwise at room temperature. The mixture was then stirred at room temperature for 1 h. After it was confirmed by TLC that the reaction was completed, the mixture was concentrated under reduced pressure to obtain the target compound as a light yellow oil. LC-MS(ES+): 328 (M+H)+

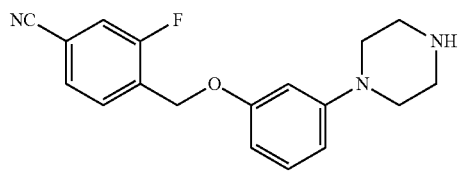 [SMILES: N#Cc1ccc(COc2cccc(N3CCNCC3)c2)c(F)c1]

(3) Synthesis of Intermediate 3: 6-(((6-(piperazin-1-yl)pyridin-2-yl)oxy)methyl)nicotinonitrile The intermediate 3 was synthesized according to the Preparation Method 1.

1) Synthesis of 4-((3-bromophenoxy)methyl)-3-fluorobenzonitrile

By using 4-(bromomethyl)-3-fluorobenzonitrile (10 g), 3-bromophenol (5.46 mL) and potassium carbonate (9.68 g), and $CH_3CN$ (100 mL), the target compound (11.88 g, 83%) was obtained. LC-MS(ES+): 307 (M+H)+

2) Synthesis of tert-butyl 4-(3-((4-cyano-2-fluorobenzyl)oxy)phenyl)piperazine-1-carboxylate The compound (2.45 g) synthesized in the step 1), 1-Boc-piperazine (1.79 g), $Pd_2(dba)_3$ (367 mg), BINAP (498 mg), and $Cs_2CO_3$ (5.21 g) in toluene (40 mL) were reacted for 14 h to obtain the target compound (668 mg) at a yield of 20%. LC-MS(ES+): 412 (M+H)+

3) Synthesis of 3-fluoro-4-((3-(piperazin-1-yl)phenoxy)methyl)benzonitrile

The compound (411 mg) synthesized in the step 2) was dissolved in DCM (5 mL). TFA (5 mL) was added. The resulting mixture was stirred at room temperature for 1.5 h. After it was confirmed by TLC that the reaction was completed, the mixture was concentrated under reduced pressure. Diethyl ether was added. The resulting residue was triturated to obtain the target compound (410 mg, 81%). LC-MS(ES+): 312 (M+H)+

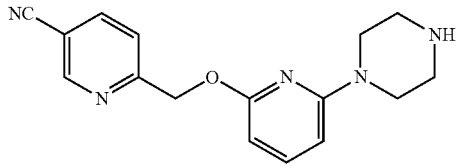 [SMILES: N#Cc1ccc(COc2cccc(N3CCNCC3)n2)nc1]

(4) Synthesis of Intermediate 4: 6-(((6-(piperazin-1-yl)pyridin-2-yl)oxy)methyl)nicotinonitrile The intermediate 4 was synthesized according to the Preparation Method 1.

1) Synthesis of 6-(((6-chloropyridin-2-yl)oxy)methyl)nicotinonitrile 6-(bromomethyl)nicotinonitrile (1.52 g) and 6-chloro-2-hydroxy pyridine (1.0 g) were placed in a round bottom flask and stirred in toluene (50 mL). $Ag_2CO_3$ (4.26 g) was added to the mixture. The resulting mixture was heated to 100° C. and then stirred for 1 d. After it was confirmed by TLC that the reaction was completed, the mixture was diluted with EA and filtered through a celite pad to obtain a filtrate. The filtrate was concentrated under reduced pressure. The residue was purified by silica gel column chromatography with hexane/ethyl acetate to obtain the target compound (1.55 g, 82%). LC-MS(ES+): 246 (M+H)+

2) Synthesis of tert-butyl 4-(6-((5-cyanopyridin-2-yl)methoxy)pyridin-2-yl)piperazine-1-carboxylate The compound (600 mg) synthesized in the step 1), 1-Boc-piperazine (500 mg), $Pd_2(dba)_3$ (112 mg), $Cs_2CO_3$ (1.6 g), and BINAP (152 mg) were placed in a round bottom flask and stirred in toluene (20 mL). The mixture was heated to 120° C. under nitrogen and stirred for 1 d. After it was confirmed by TLC that the reaction was completed, the mixture was diluted with EA and filtered through a celite pad to obtain a filtrate. The filtrate was concentrated under reduced pressure. The residue was purified by silica gel column chromatography with hexane/ethyl acetate to obtain the target compound (751 mg, 78%) as a transparent syrup. LC-MS(ES+): 396 (M+H)+

3) Synthesis of 6-(((6-(piperazin-1-yl)pyridin-2-yl)oxy) methyl)nicotinonitrile

The compound (751 mg) synthesized in the step 2) was placed in a round bottom flask, dissolved in DCM (10 mL), and stirred. TFA (1 mL) was dropwise added to the mixture at 0° C. while the mixture was stirred. The resulting mixture was then stirred at room temperature for 6 h. After it was confirmed by TLC that the reaction was completed, the mixture was neutralized with a sat. aqueous NaHCO3 solution, extracted with a DCM/MeOH 10% solution, dried over anhydrous magnesium sulfate, and filtered under reduced pressure. The resulting filtrate was concentrated under reduced pressure to obtain the target compound (600 mg) as a brown solid. LC-MS(ES+): 296 (M+H)+

2. Preparation Method 2

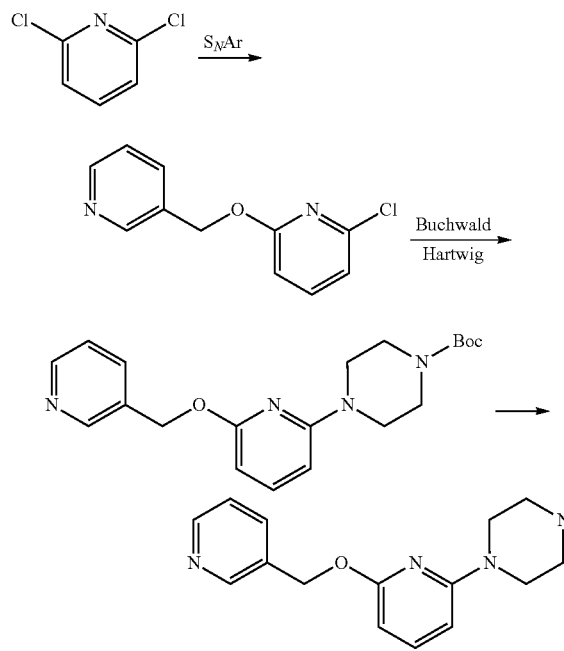

(1) Synthesis of Intermediate 5: 1-(6-(pyridin-3-ylmethoxy)pyridin-2-yl)piperazine 1) Synthesis of 2-chloro-6-(pyridin-3-ylmethoxy)pyridine 3-pyridinemethanol (885 mg) was placed in a round bottom flask and stirred in THF (17 mL). KOtBu (1.37 g) was added portionwise to the mixture. The resulting mixture was stirred for 30 mins. Subsequently, 2,6-chloropyridine (1000 mg) was added to the mixture, and the resulting mixture was stirred at room temperature for 1 d. After it was confirmed by TLC that the reaction was completed, the mixture was added to a mixture of sat. aqueous NH4Cl solution and EA. The resulting mixture was then stirred for 15 mins. The resulting mixture was filtered through a celite pad and extracted with EA. The resulting organic layer was dried over anhydrous magnesium sulfate and filtered under reduced pressure. The resulting filtrate was concentrated under reduced pressure. The residue was purified by silica gel column chromatography with hexane/ethyl acetate to obtain the target compound (1.20 g, 86%) as a white solid LC-MS(ES+): 221 (M+H)+

2) Synthesis of tert-butyl 4-(6-(pyridin-3-ylmethoxy)pyridin-2-yl)piperazine-1-carboxylate The compound (441 mg) synthesized in the step 1), 1-Boc-piperazine (559 mg), Pd2(dba)3 (92 mg), BINAP (125 mg), and Cs2CO3 (1.30 g) were placed in a round bottom flask and stirred in toluene (6 mL). Under nitrogen, the mixture was heated to 90° C. and stirred for 1 d. After it was confirmed by TLC that the reaction was completed, the mixture was filtrated with a celite pad. The resulting filtrate was concentrated under reduced pressure. The residue was purified by silica gel column chromatography with hexane/ethyl acetate to obtain the target compound (225 mg, 31%). LC-MS(ES+): 371 (M+H)+

3) Synthesis of 1-(6-(pyridin-3-ylmethoxy)pyridin-2-yl) piperazine

Acetyl chloride (0.3 mL) was slowly added dropwise to a mixed solvent of ethanol (0.4 mL) and EA (3 mL), and the mixture was stirred at 40° C. for 1 h. The compound (225 mg) synthesized in the step 2) was added to the mixture, and the resulting mixture was stirred at 40° C. for 2 h. EA was added to the mixture, the resulting mixture was vehemently stirred at room temperature for 1 h and filtered to obtain a solid. The solid was dissolved in 5% MC/MeOH solution. Sat. aqueous Na2CO3 solution was added, and the resulting mixture was stirred for 30 mins. The organic layer obtained from layer separation was dried over anhydrous magnesium sulfate, filtered, and concentrated to obtain the target compound (135 mg, 86%). LC-MS(ES+): 271 (M+H)+

3. Preparation Method 3

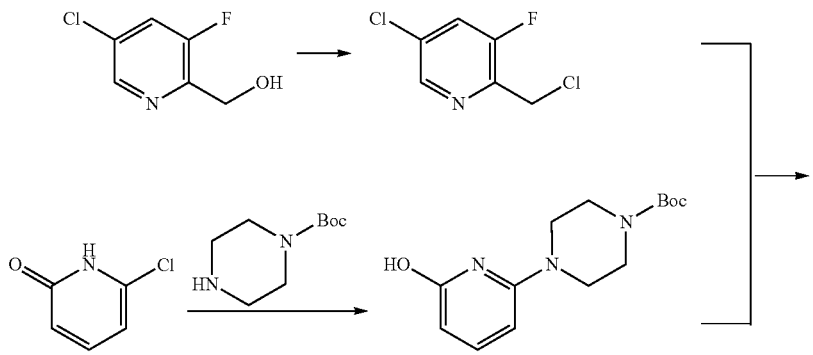

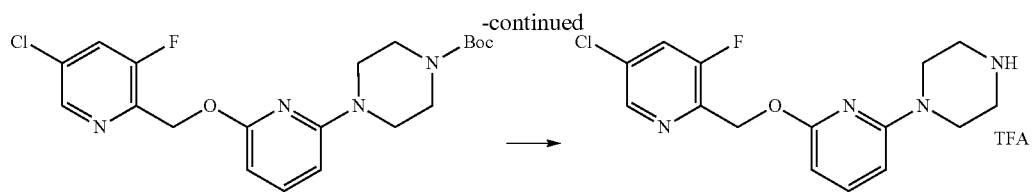

(1) Synthesis of Intermediate 6: 1-(6-((5-chloro-3-fluoropyridin-2-yl)methoxy)pyridin-2-yl)piperazine trifluoroaceticacid salt 1) Synthesis of 5-chloro-2-(chloromethyl)-3-fluoropyridine (5-chloro-3-fluoropyridin-2-yl)methanol (324 mg) was dissolved in DCM (20 mL), and the mixture was cooled to 0° C. $SOCl_2$ (0.3 mL) was slowly added to the mixture, and the mixture was stirred at room temperature for 3 h. After it was confirmed by TLC that the reaction was completed, the resulting mixture was concentrated under reduced pressure to obtain the target compound. The target compound was used in the next step below without further purification. LC-MS(ES$^+$): 181 (M+H)$^+$ 2) Synthesis of tert-butyl 4-(6-hydroxypyridin-2-yl)piperazine-1-carboxylate 6-chloropyridin-2(1H)-one (2 g) and N-Boc-piperazine (7.2 g) were dissolved in n-butanol (16 mL). The mixture was stirred at 140° C. for 3 d. Aq. $NH_4Cl$ and brine were added to the mixture. The resulting mixture was extracted with EA twice. The resulting organic layer was dried over anhydrous $Na_2SO_4$, filtered, and concentrated under reduced pressure. The resulting residue was diluted with $CH_3CN$ (40 mL) and $H_2O$ (200 mL) and stirred at room temperature for 2 h. Then, the resulting mixture was filtered to obtain the target compound (1.49 g, 35%) as a solid. LC-MS(ES$^+$): 280 (M+H)$^+$ 3) Synthesis of tert-butyl 4-(6-((5-chloro-3-fluoropyridin-2-yl)methoxy)pyridin-2-yl)piperazine-1-carboxylate Tert-butyl 4-(6-hydroxypyridin-2-yl)piperazine-1-carboxylate (559 mg) was dissolved in $CH_3CN$ (5 mL). 5-chloro-2-(chloromethyl)-3-fluoropyridine (2 mmol) and potassium carbonate (553 mg) were added to the mixture, and the mixture was stirred at 40° C. for 14 h. After it was confirmed by TLC that the reaction was completed, the mixture was diluted with distilled $H_2O$ and was extracted with EA twice. The resulting organic layer was dried over anhydrous $Na_2SO_4$, filtered, and concentrated under reduced pressure. The residue was purified by silica gel column chromatography with hexane/ethyl acetate to obtain the target compound (249 mg, 29%) as a yellow liquid. LC-MS (ES$^+$): 423 (M+H)$^+$ 4) Synthesis of 1-(6-((5-chloro-3-fluoropyridin-2-yl)methoxy)pyridin-2-yl)piperazine trifluoroaceticacid salt The compound (220 mg) synthesized in the step 3) was dissolved in DCM (10 mL). TFA (10 mL) was added to the mixture, and the mixture was stirred at room temperature for 1.5 h. After it was confirmed by TLC that the reaction was completed, the mixture was concentrated under reduced pressure to obtain the target compound, which was used without further purification. LC-MS(ES$^+$): 323 (M+H)$^+$ 4. Preparation Method 4

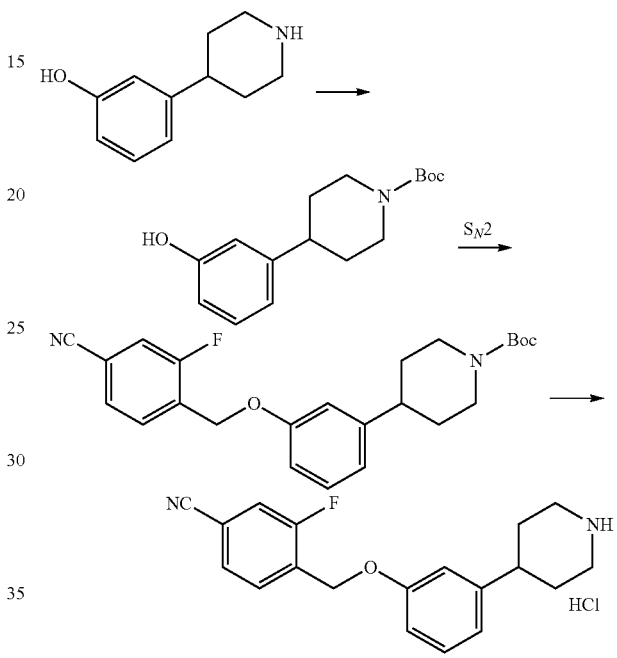

(1) Synthesis of Intermediate 7: 3-fluoro-4-(((6-(piperidin-4-yl)pyridin-2-yl)oxy)methyl)benzonitrile hydrogenchloride salt 1) Synthesis of tert-butyl 4-(3-hydroxyphenyl)piperidine-1-carboxylate 3-(piperidin-4-yl)phenol (1 mmol) and (Boc)$_2$O (1 mmol) were placed in a round bottom flask, dissolved in DCM (2 mL), and stirred at room temperature for 1 h. After it was confirmed by TLC that the reaction was completed, the mixture was diluted with water and extracted with DCM. The resulting organic layer was dried over anhydrous magnesium sulfate, filtered, and concentrated under reduced pressure. The target compound was obtained and used without further purification. LC-MS (ES$^+$): 278 (M+H)$^+$ 2) Synthesis of tert-butyl 4-(6-((4-cyano-2-fluorobenzyl)oxy)pyridin-2-yl)piperidine-1-carboxylate The compound (1 eq.) synthesized in the step 1) and 4-(bromomethyl)-3-fluorobenzonitrile (1 eq.) were placed in a round bottom flask and stirred in $CH_3CN$ (0.1 M). After potassium carbonate (1.5 eq.) was added, the mixture was stirred at 50° C. for 2 h. After it was confirmed by TLC that the reaction was completed, the mixture was added to an appropriate amount of water and extracted with EA. The resulting organic layer was washed with brine solution, dried over anhydrous magnesium sulfate, filtrated under reduced pressure, and concentrated under reduced pressure. The residue was purified by silica gel column chromatography to obtain the target compound (70%) as a colorless liquid. LC-MS(ES$^+$): 412 (M+H)$^+$ 3) Synthesis of 3-fluoro-4-(((6-(piperidin-4-yl)pyridin-2-yl)oxy)methyl)benzonitrile hydrogenchloride salt The compound (560 mg) synthesized in the step 2) was dissolved in 1,4-dioxane (4 mL). 4 N HCl 1,4-dioxane solution (2.6 mL) was added at room temperature. The mixture was stirred for 4 h. The mixture was then concentrated under reduced pressure, and the resulting residue was treated with MTBE to obtain a solid. The solid was triturated with MTBE for 2 h. The triturated solid was filtrated and dried to obtain the target compound (85%) as a white solid. LC-MS(ES$^+$): 312 (M+H)$^+$ 5. Preparation Method 5

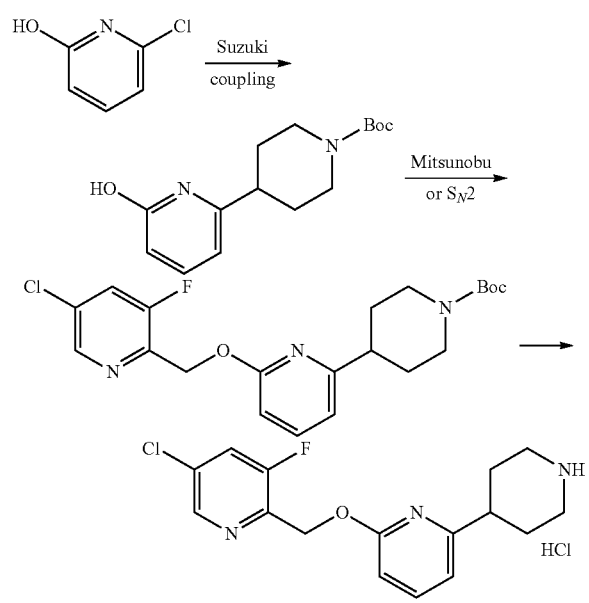

(1) Synthesis of Intermediate 8: 5-chloro-3-fluoro-2-((((6-(piperidin-4-yl)pyridin-2-yl)oxy)methyl)pyridine hydrochloride salt 1) Synthesis of tert-butyl 4-(3-hydroxyphenyl)piperidine-1-carboxylate Tert-butyl 4-(4,4,5,5-tetramethyl-1,3,2-dioxaborolain-2-yl)-3,6-dihydroxypyridin-1(2H)-carboxylate, chlorohydroxypyridine, Pd(PPh$_3$)$_4$, and Na$_2$CO$_3$ were placed in a reaction vessel equipped with a reflux condenser. 1,4-dioxane (7 mL), ethanol (3 mL), and water (1 mL) were added. The resulting mixture was heated to 120° C. under nitrogen. After being stirred for overnight, the mixture was cooled to room temperature and filtered through a celite pad using EA (50 mL). The mixture was diluted with water (20 mL), and aqueous layer was extracted with EA (3×50 mL). The resulting organic layer was dried over anhydrous magnesium sulfate, filtered under reduced pressure, and purified by column chromatography (5% MeOH/DCM) to obtain tert-butyl 6-hydroxy-3',6'-dihydro-[2,4'-bipyridine]-1'(2'H)-carboxylate as a white solid.

Tert-butyl 6-hydroxy-3',6'-dihydro-[2,4'-bipyridine]-1'(2'H)-carboxylate was dissolved in MeOH. 10% Pd/C was added. The mixture was exposed to hydrogen atmosphere (balloon pressure) at room temperature. After 2 h, it was confirmed that the reaction was not completed, and additional 10% Pd/C was added to the mixture. After 3 h, it was confirmed that the reaction was completed, and the mixture was filtered through a celite pad, washed with MeOH, and concentrated under reduced pressure. The residue was purified by column chromatography (33% ethyl acetate/hexane) to obtain the target compound (45%) as a white solid. LC-MS(ES$^+$): 278 (M+H)$^+$ 2) Synthesis of tert-butyl 4-(6-((5-chloro-3-fluoropyridin-2-yl)methoxy)pyridin-2-yl)piperidine-1-carboxylate To a solution of (5-chloro-3-fluoro-2-pyridyl)methanol, the compound synthesized in the above step 1), and toluene was added (Bu)$_3$P at room temperature. The mixture was stirred for 15 mins. ADDP was added at room temperature. The mixture was stirred at room temperature for 16 h. The mixture was poured into hexane (30 mL) and filtrated through a filter glass. The resulting organic extract was concentrated under reduced pressure. The residue was purified by silica gel column chromatography (50% ethyl acetate/hexane) to obtain the target compound (30%) as a colorless oil. LC-MS(ES$^+$): 422 (M+H)$^+$ 3) Synthesis of 5-chloro-3-fluoro-2-(((6-(piperidin-4-yl)pyridin-2-yl)oxy)methyl)pyridine hydrochloride salt The compound synthesized in the step 2) was placed in a round bottom flask and stirred in 1,4-dioxane (4 mL). 4 N HCl 1,4-dioxane solution (1 mL) was added to the mixture, and the mixture was stirred at room temperature for 1 h. The mixture was concentrated under reduced pressure to obtain the target compound as a white solid, which was used in the next step without further purification. LC-MS(ES$^+$): 322 (M+H)$^+$ 6. Preparation Method 6

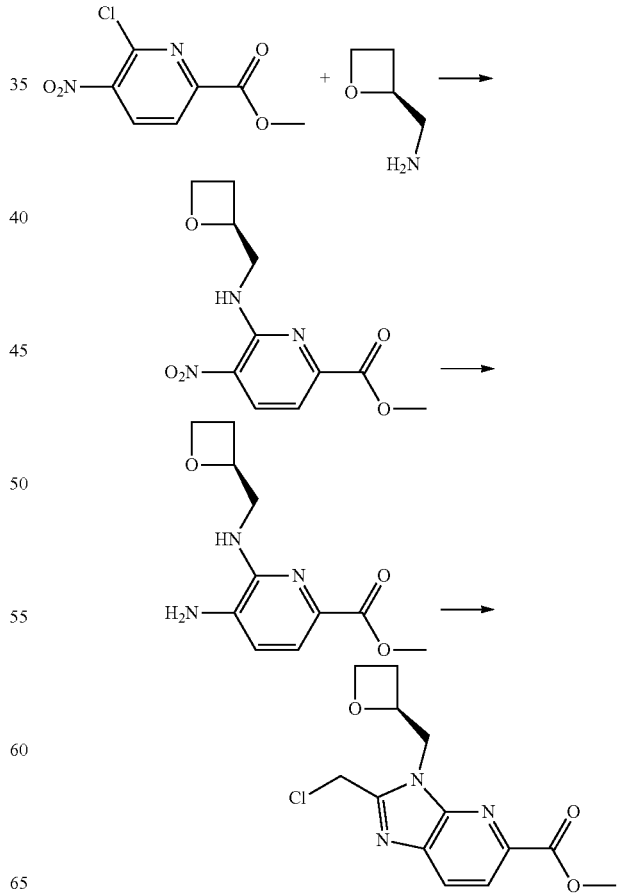

(1) Synthesis of Intermediate 9: methyl (S)-2-(chloromethyl)-3-(oxetan-2-ylmethyl)-3H-imidazo[4,5-b]pyridine-5-carboxylate

1) Synthesis of methyl (S)-5-nitro-6-((oxetan-2-ylmethyl)amino)picolinate

Methyl 6-chloro-5-nitropicolinate (1.0 g), TEA (1.93 mL), and (S)-oxetan-2-ylmethanamine (402 mg) were dissolved in DMF (10 mL), and the resulting mixture was stirred at room temperature for overnight. The mixture was concentrated to remove THF, diluted with EA, and washed with brine solution (×2). The resulting organic layer was dried over anhydrous sodium sulfate, filtered, concentrated, and purified by column chromatography to obtain the target compound (1.1 g, 89%) as a yellow solid. LC-MS(ES+): 268 (M+H)+

2) Synthesis of methyl (S)-5-amino-6-((oxetan-2-ylmethyl)amino)picolinate

The compound (1.1 g) synthesized in the step 1) and Pd/C (110 mg) were added to MeOH (3.8 mL), and the mixture was stirred at room temperature for 3 h. The mixture was filtered through a celite pad to remove a metal catalyst, and the resulting filtrate was concentrated to obtain the target compound (1.0 g, 100%) as a white solid. LC-MS(ES+): 238 (M+H)+

3) Synthesis of methyl (S)-2-(chloromethyl)-3-(oxetan-2-ylmethyl)-3H-imidazo[4,5-b]pyridine-5-carboxylate The compound (1.0 g) synthesized in the step 2) and chloroacetic anhydride (754 mg) were added to THF (21 mL), and the mixture was stirred at 60° C. for 1.5 h. The mixture was concentrated to remove THF, and EA and sat. aqueous NaHCO3 solution were added. The resulting mixture was extracted with EA (×2). The resulting organic layer was washed with brine, dried over anhydrous sodium sulfate, filtered, and concentrated. The residue was purified by column chromatography to obtain the target compound (760 mg, 61%) as a white solid. LC-MS(ES+): 296 (M+H)+

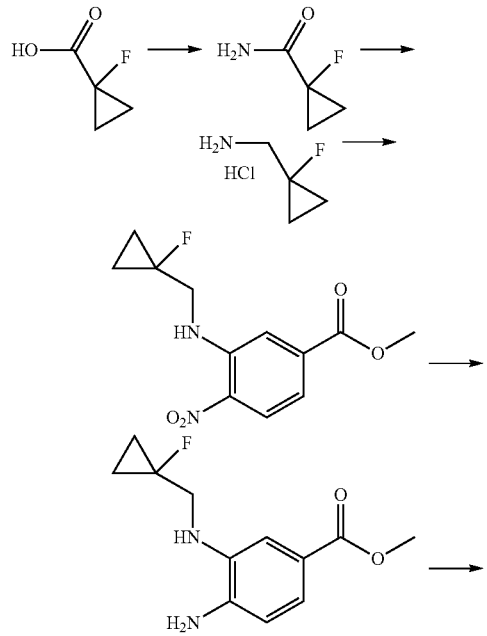

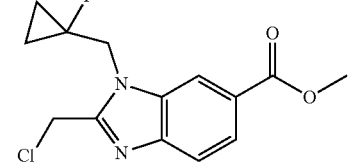

(2) Synthesis of Intermediate 10: methyl 2-(chloromethyl)-1-((1-fluorocyclopropyl)methyl)-1H-benzo[d]imidazole-6-carboxylate

1) Synthesis of 1-fluorocyclopropane-1-carboxamide 1-fluorocyclopropane-1-carboxylic acid (38, 4.0 g) was added to thionyl chloride (1.8 mL), and the mixture was stirred under reflux for 30 mins. The mixture was concentrated under reduced pressure to obtain 1-fluoropropane-1-carbonyl chloride as a liquid state, which was used for the next step without further purification. In a separate reaction flask, 28% aqueous ammonia solution (10 mL) and THF (2 mL) were mixed. Then, 1-fluoropropane-1-carbonyl chloride (38.4 mmol) solution was slowly added dropwise to the mixture at 0° C. The resulting mixture was stirred in an open flask state overnight. The resulting white solid was filtered, washed with ice water, and dried to obtain the target compound (500 mg) as a light yellow solid. LC-MS(ES+): 104 (M+H)+

2) Synthesis of (1-fluorocyclopropyl)methanamine hydrochloride salt

The compound (270 mg) synthesized in the step 1) was dissolved in THF (5 mL), and 1 M BH3 THF solution (10.4 mL) was added at 0° C. The mixture was stirred at 70° C. for overnight. 10% HCl solution (2 mL) was slowly added at 0° C. The mixture was stirred at room temperature for 1 h. The mixture was concentrated under reduced pressure, washed with Et2O, neutralized to pH 10 with 10% NaOH aqueous solution, and extracted with Et2O (×3). The resulting organic layer was dried over anhydrous magnesium sulfate and concentrated under reduced pressure. 1.5 mL of 2 N HCl in Et2O solution was dropwise added at 0° C. The resulting mixture was stirred at room temperature for 1 h and filtrated to obtain the target compound (102 mg, 31%) as a green solid without further purification. LC-MS(ES+): 90 (M+H)+

3) Synthesis of methyl 3-(((1-fluorocyclopropyl)methyl)amino)-4-nitrobenzoate The compound (100 mg) synthesized in the step 2) and methyl 3-fluoro-4-nitrobenzoate (158 mg) were dissolved in CH3CN (2.5 mL), and TEA (0.33 mL) was added dropwise. The mixture was stirred at 85° C. for overnight. The mixture was concentrated under reduced pressure, separated, and purified by column chromatography (12 g SiO2, 20% EA→50% EA) to obtain the target compound (119 mg, 56%) as a white solid. LC-MS(ES+): 269 (M+H)+

4) Synthesis of methyl 4-amino-3-(((1-fluorocyclopropyl)methyl)amino)benzoate The compound (100 mg) synthesized in the step 3) was dissolved in THF (5 mL), and Pd/C (118 mg) was added. The mixture was stirred at room temperature for 3 h under hydrogen gas. The mixture was filtered and concentrated under reduced pressure to obtain the target compound (71 mg, 80%) as a white solid. LC-MS(ES+): 239 (M+H)+

5) Synthesis of methyl 2-(chloromethyl)-1-((1-fluorocyclopropyl)methyl)-1H-benzo[d]imidazole-6-carboxylate The compound (70 mg) synthesized in the step 4) and 2-chloro-1,1,1-trimethoxyethane (0.04 mL) were dissolved in CH₃CN (3 mL), and p-TSA (3 mg) was added. The mixture was stirred at 85° C. for 3 h. The mixture was concentrated under reduced pressure and purified by column chromatography (12 g SiO$_2$, 20% EA→50% EA) to obtain the target compound (89 mg, 52%) as a white solid. LC-MS (ES$^+$): 297 (M+H)$^+$ Synthesis of Intermediates 11 to 19

The compounds listed as intermediates 11 to 19 in Table 1 below were prepared by using procedures identical or analogous to the Preparation Methods 1 to 6 from appropriate starting materials which are available commercially or may be prepared by methods known in the art. The compounds were purified using methods known to those skilled in the art, which may include silica gel chromatography, HPLC, or recrystallization. The final compounds could be isolated as neutrals or as acid addition or base addition salts. The compound names and LC-MS data of the prepared intermediates are shown in Table 1 below.

Table 1

TABLE 1

| Intermediate No. | Preparation Method | Structure | Compound name | LC-MS data (ES+) |
|---|---|---|---|---|
| 11 | 1 | | 6-(((6-(piperazin-1-yl)pyrazin-2-yl)oxy)methyl)nicotinonitrile trifluoroaceticacid salt | 297 (M + H)$^+$ |
| 12 | 1 | | 6-((3-(piperazin-1-yl)phenoxy)methyl)nicotinonitrile trifluoroaceticacid salt | 295 (M + H)$^+$ |
| 13 | 2 | 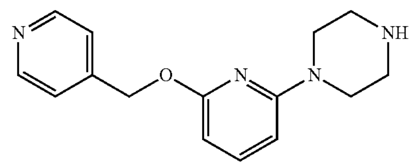 [SMILES: c1cc(OCc2ccncc2)nc(N2CCNCC2)c1] | 1-(6-(pyridin-4-ylmethoxy)pyridin-2-yl)piperazine | 271 (M + H)$^+$ |
| 14 | 2 | 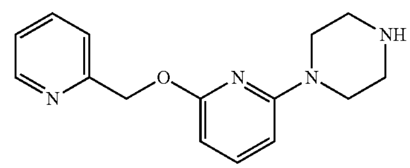 [SMILES: c1ccc(COc2cccc(N3CCNCC3)n2)nc1] | 1-(6-(pyridin-2-ylmethoxy)pyridin-2-yl)piperazine | 271 (M + H)$^+$ |
| 15 | 3 | 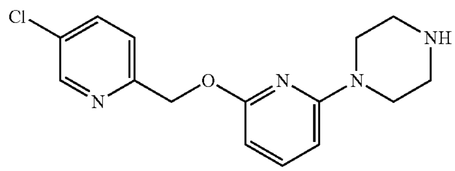 [SMILES: Clc1ccc(COc2cccc(N3CCNCC3)n2)nc1] | 1-(6-((5-chloropyridin-2-yl)methoxy)pyridin-2-yl)piperazine | 305 (M + H)$^+$ |
| 16 | 5 | | 6-(((6-(piperidin-4-yl)pyridin-2-yl)oxy)methyl)nicotinonitrile hydrochloride salt | 295 (M + H)$^+$ |
| 17 | 5 | | 5-chloro-3-fluoro-2-((3-(piperidin-4-yl)phenoxy)methyl)pyridine hydrochloride salt | 321 (M + H)$^+$ |
| 18 | 6 | 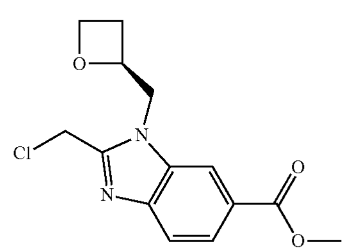 [SMILES: COC(=O)c1ccc2nc(CCl)n(C[C@@H]3CCO3)c2c1] | methyl (S)-2-(chloromethyl)-1-(oxetan-2-ylmethyl)-1H-benzo[d]imidazole-6-carboxylate | 295 (M + H)$^+$ |

TABLE 1-continued

| Intermediate No. | Preparation Method | Structure | Compound name | LC-MS data (ES+) |
|---|---|---|---|---|
| 19 | 6 | 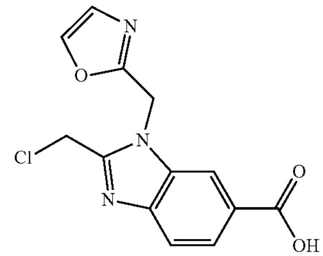 [SMILES: O=C(O)c1ccc2nc(CCl)n(Cc3ncco3)c2c1] | methyl 2-(chloromethyl)-1-(oxazol-2-ylmethyl)-1H-benzo[d]imidazole-6-carboxylate | 292 (M + H)+ |

EXAMPLES

Synthesis of the compounds of Examples 1 to 18 using the intermediates above will be described in detail below. The following Preparation Examples A, B, and C show exemplary methods of synthesizing the compounds of Examples 1 to 18 using the intermediates above. Using the Preparation Examples A, B and C, those skilled in the art may prepare the compounds of Examples 1 to 18 of the present disclosure.

1. Preparation Example A

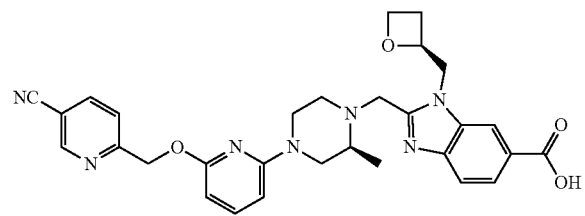 [SMILES: C[C@H]1CN(c2cccc(OCc3ccc(C#N)cn3)n2)CCN1Cc1nc2ccc(C(=O)O)cc2n1C[C@@H]1CCO1]

(1) Synthesis of Example 1: 2-(((S)-4-(6-((5-cyano-pyridin-2-yl)methoxy)pyridin-2-yl)-2-methylpiper-azin-1-yl)methyl)-1-(((S)-oxetan-2-yl)methyl)-1H-benzo[d]imidazole-6-carboxylic acid 1) Synthesis of methyl 2-(((S)-4-(6-((5-cyanopyridin-2-yl)methoxy)pyridin-2-yl)-2-methylpiperazin-1-yl)methyl)-1-(((S)-oxetan-2-yl)methyl)-1H-benzo[d]imidazole-6-carboxylate Intermediate 1 (194 mg), intermediate 18 (185 mg), and potassium carbonate (350 mg) were dissolved in $CH_3CN$ (10 mL) in a round bottom flask, and the mixture was stirred at 60° C. for one day. After it was confirmed by TLC that the reaction was completed, the mixture was diluted with EA, and the resulting organic layer was washed using sat. aqueous $NaHCO_3$, sat. aqueous $NH_4Cl$, and brine successively in the order. Then, the organic layer was dried over anhydrous magnesium sulfate and filtered under reduced pressure to obtain a filtrate. The filtrate was concentrated under reduced pressure. The residue was purified by silica gel column chromatography with a hexane/ethyl to obtain methyl 2-(((S)-4-(6-((5-cyanopyridin-2-yl)methoxy)pyridin-2-yl)-2-methylpiperazin-1-yl)methyl)-1-(((S)-oxetan-2-yl)methyl)-1H-benzo[d]imidazole-6-carboxylate (241 mg, 67%) as a transparent syrup. LC-MS(ES+): 568 (M+H)+

2) Synthesis of the Final Compound

The compound (241 mg) obtained in the step 1) was dissolved in $CH_3CN$ (10 mL) in a round bottom flask, and the mixture was stirred. While the mixture was stirred, 1.0 M TBD aqueous solution (0.85 mL) was added dropwise. Purified water (1 mL) was added to the mixture, and the mixture was stirred at 60° C. for one day. After it was confirmed by TLC that the reaction was completed, the mixture was neutralized to pH 7 with 1 N HCl aqueous solution. The resulting mixture was extracted with DCM/MeOH 10% solution, dried over anhydrous magnesium sulfate, and filtered under reduced pressure to obtain a filtrate. The filtrate was concentrated under reduced pressure. The residue was purified by silica gel column chromatography with DCM/MeOH to obtain the final compound (55 mg, 24%) as a pale green solid. $^1$H NMR (DMSO-$d_6$): δ 8.97 (s, 1H), 8.27 (d, J=2.0 Hz, 1H), 8.26 (s, 1H), 7.81 (d, J=8.4 Hz, 1H), 7.64 (d, J=8.4 Hz, 1H), 7.53 (d, J=8.4 Hz, 1H), 7.47 (t, J=8.0 Hz, 1H), 6.31 (d, J=8.4 Hz, 1H), 6.16 (d, J=7.6 Hz, 1H), 5.40 (s, 2H), 5.14 (m, 1H), 4.73 (m, 2H), 4.47-4.46 (m, 1H), 4.34-4.25 (m, 2H), 3.70-3.59 (m, 4H), 2.90 (t, J=10.0 Hz, 1H), 2.72-2.61 (m, 3H), 2.38-2.33 (m, 1H), 2.26-2.21 (m, 1H), 1.03 (d, J=6.0 Hz, 3H); LC-MS (ES+): 554 [M+H]+.

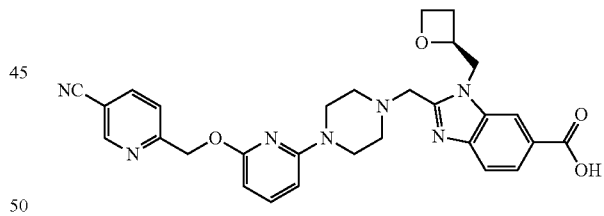

(2) Synthesis of Example 2: (S)-2-((4-(6-((5-cyano-pyridin-2-yl)methoxy)pyridin-2-yl)piperazin-1-yl) methyl)-1-(oxetan-2-ylmethyl)-1H-benzo[d]imida-zole-6-carboxylic acid 1) Synthesis of methyl (S)-2-((4-(6-((5-cyanopyridin-2-yl)methoxy)pyridin-2-yl)piperazin-1-yl)methyl)-1-(oxetan-2-ylmethyl)-1H-benzo[d]imidazole-6-carboxylate Intermediate 4 (233 mg), intermediate 18 (232 mg), potassium carbonate (436 mg) were dissolved in $CH_3CN$ (10 mL) in a round bottom flask, and the mixture was stirred at 60° C. for one day. After it was confirmed by TLC that the reaction was completed, the mixture was diluted with EA, and the resulting organic layer was washed using sat. aqueous $NaHCO_3$, sat. aqueous $NH_4Cl$, and brine successively. Then, the organic layer was dried over anhydrous magnesium sulfate and filtered under reduced pressure to obtain a filtrate. The filtrate was concentrated under reduced pressure. The residue was purified by silica gel column chromatography with a hexane/ethyl to obtain methyl (S)-2-((4-(6-((5-cyanopyridin-2-yl)methoxy)pyridin-2-yl)piperazin-1-yl)methyl)-1-(oxetane-2-ylmethyl)-1H-benzo[d]imidazole-6-carboxylate (390 mg, 89%) as a transparent syrup. LC-MS(ES$^+$): 554 (M+H)$^+$ 2) Synthesis of the Final Compound The compound (387 mg) obtained in the step 1) was dissolved in CH$_3$CN (10 mL) in a round bottom flask, and the mixture was stirred. While the mixture was stirred, 1.0 M TBD aqueous solution (1.4 mL) was added dropwise. Purified water (0.6 mL) was added to the mixture, and the mixture was stirred at 60° C. for 1 d. After it was confirmed by TLC that the reaction was completed, the mixture was neutralized to pH 7 with 1 N HCl aqueous solution, extracted with DCM/MeOH 10% solution, dried over anhydrous magnesium sulfate, and filtered under reduced pressure to obtain a filtrate. The filtrate was concentrated under reduced pressure. The residue was purified by silica gel column chromatography with DCM/MeOH to obtain the final compound (225 mg, 60%) as a pale green solid. $^1$H NMR (DMSO-d$_6$): δ 8.97 (s, 1H), 8.28 (d, J=8.2 Hz, 1H), 8.24 (s, 1H), 7.80 (d, J=2.8 Hz, 1H), 7.62 (d, J=8.4 Hz, 1H), 7.56 (d, J=7.6 Hz, 1H), 7.49 (t, J=8.0 Hz, 1H), 6.32 (d, J=8.0 Hz, 1H), 6.18 (d, J=8.0 Hz, 1H), 5.41 (s, 2H), 5.11-5.05 (m, 1H), 4.79 (d, J=7.2 Hz, 1H), 4.75 (d, J=7.2 Hz, 1H), 4.65-4.60 (m, 1H), 4.50-4.45 (m, 1H), 4.39-4.34 (m, 1H), 3.94 (d, J=13.2 Hz, 1H), 3.76 (d, J=13.2 Hz, 1H), 3.34-3.29 (m, 3H, assumed; partially obscured by water peak), 2.66 (m, 1H), 2.50-2.42 (m, 6H, assumed; partially obscured by solvent peak); LC-MS(ES$^+$): 540 (M+H)$^+$

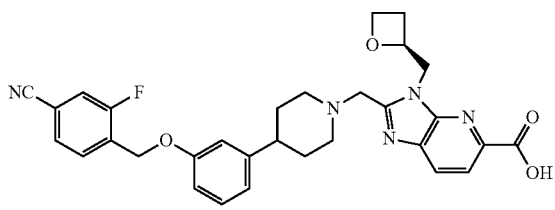 [SMILES: N#Cc1ccc(COc2cccc(C3CCN(Cc4nc5ccc(C(=O)O)nc5n4C[C@@H]4CCO4)CC3)c2)c(F)c1]

Synthesis of Example 3: (S)-2-(4-(3-((4-cyano-2-fluorobenzyl)oxy)phenyl)piperidin-1-yl)methyl)-3-(oxetan-2-ylmethyl)-3H-imidazo[4,5-b]pyridine-5-carboxylic acid 1) Synthesis of methyl (S)-2-((4-(3-((4-cyano-2-fluorobenzyl)oxy)phenyl)piperidin-1-yl)methyl)-3-(oxetane-2-ylmethyl)-3H-imidazo[4,5-b]pyridine-5-carboxylate Intermediate 7 (1.0 eq.), intermediate 9 (1.0 eq.), and potassium carbonate (3.0 eq.) were dissolved in CH$_3$CN (0.1 M) in a round bottom flask, and the mixture was stirred at room temperature for 3 d. After it was confirmed by TLC that the reaction was completed, purified water was added to the mixture. The mixture was extracted with EA, and the resulting organic layer was washed with brine, dried over anhydrous magnesium sulfate, filtered, and concentrated under reduced pressure. The residue was purified by silica gel column chromatography to obtain methyl (S)-2-((4-(3-((4-cyano-2-fluorobenzyl)oxy)phenyl)piperidin-1-yl)methyl)-3-(oxetane-2-ylmethyl)-3H-imidazo[4,5-b]pyridine-5-carboxylate (91%). LC-MS(ES$^+$): 570 (M+H)$^+$ 2) Synthesis of the Final Compound The compound obtained in the step 1) was dissolved in CH$_3$CN (0.1 M) in a round bottom flask, and the mixture was stirred. After 1.0 M TBD aqueous solution was added, the mixture was stirred at 50° C. for 4 hours. After it was confirmed by TLC that the reaction was completed, the mixture was acidified to pH 6 with 2 M citric acid aqueous solution (7.0 mL) and diluted with purified water. The resulting aqueous layer was extracted with DCM/MeOH 5% solution. The organic layer was dried over anhydrous magnesium sulfate, filtered, and concentrated under reduced pressure. The residue was purified by silica gel column chromatography with DCM/MeOH to obtain the final compound (55%) as a pale yellow solid. $^1$H NMR (400 MHz, DMSO-d$_6$) δ 13.08-12.98 (m, 1H), 8.16-8.13 (m, 1H), 8.01-7.90 (m, 2H), 7.77-7.75 (m, 2H), 7.22 (t, J=7.9 Hz, 1H), 6.94-6.84 (m, 3H), 5.23-5.21 (m, 3H), 4.87 (dd, J=14.6, 6.3 Hz, 1H), 4.74 (dd, J=14.6, 4.2 Hz, 1H), 4.53-4.46 (m, 1H), 4.41-4.34 (m, 1H), 4.03-3.91 (m, 2H), 2.95 (dd, J=15.1, 12.8 Hz, 2H), 2.75-2.65 (m, 1H), 2.30-2.18 (m, 2H), 1.80-1.63 (m, 4H); LC-MS(ES$^+$): 556 (M+H)$^+$

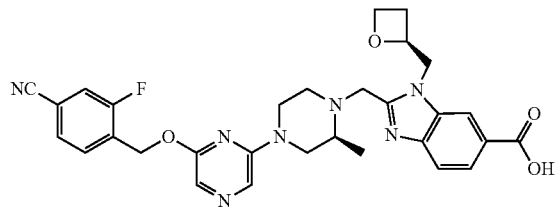 [SMILES: C[C@H]1CN(c2cncc(OCc3ccc(C#N)cc3F)n2)CCN1Cc1nc2ccc(C(=O)O)cc2n1C[C@@H]1CCO1]

(4) Synthesis of Example 4: 2-(((S)-4-(6-((4-cyano-2-fluorobenzyl)oxy)pyrazin-2-yl)-2-methylpiperazin-1-yl)methyl)-1-(((S)-oxetan-2-yl)methyl)-1H-benzo[d]imidazole-6-carboxylic acid 1) Synthesis of methyl 2-(((S)-4-(6-((4-cyano-2-fluorobenzyl)oxy)pyrazin-2-yl)-2-methylpiperazin-1-yl)methyl)-1-(((S)-oxetan-2-yl)methyl)-1H-benzo[d]imidazole-6-carboxylate Intermediate 2 (1.0 eq), intermediate 18 (1.0 eq), and potassium carbonate (5.0 eq) were dissolved in CH$_3$CN (0.1 M) in a round bottom flask, and the mixture was stirred at room temperature for 2 days. It was identified that intermediate 2 remained as the reaction was not completed. Thus, 0.5 eq of intermediate 18 was added to the mixture, and the mixture was heated to 60° C. After it was confirmed by TLC that the reaction was completed, the mixture was cooled to room temperature, and purified water was added. The mixture was extracted with EA, and the resulting organic layer was washed with brine. Then, the organic layer was dried over anhydrous magnesium sulfate, filtered, and concentrated under reduced pressure. The residue was purified by silica gel column chromatography with a hexane/ethyl to obtain methyl 2-(((S)-4-(6-((4-cyano-2-fluorobenzyl)oxy)pyrazin-2-yl)-2-methylpiperazin-1-yl)methyl)-1-(((S)-oxetan-2-yl)methyl)-1H-benzo[d]imidazole-6-carboxylate (70%) as a colorless liquid. LC-MS (ES$^+$): 586 (M+H)$^+$ 2) Synthesis of the Final Compound The compound obtained in the step 1) was placed in a round bottom flask and was stirred in CH$_3$CN (0.1 M). After 1.0 M TBD aqueous solution was added, the mixture was stirred at 60° C. for 3 hours. After it was confirmed by TLC that the reaction was completed, the mixture was acidified to pH 6 with 2 M citric acid aqueous solution (7.0 mL) and diluted with purified water. The mixture was extracted with DCM/MeOH 5% solution. The resulting organic layer was dried over anhydrous magnesium sulfate, filtered, and concentrated under reduced pressure. The residue was purified by silica gel column chromatography with DCM/MeOH to obtain the final compound. The purity was not enough with MPLC. Thus, further separation was performed using PTLC (7% DCM/MeOH) to obtain the final compound (26%) as a yellow foam. $^1$H NMR (400 MHz, DMSO-$d_6$) δ 12.83 (brs, 1H), 8.28 (d, J=0.8 Hz, 1H), 7.89 (dd, J=9.2, 1.2 Hz, 1H), 7.84 (s, 1H), 7.82 (dd, J=8.4, 1.6 Hz, 1H), 7.73-7.65 (m, 3H), 7.53 (s, 1H), 5.43 (s, 2H), 5.18-5.15 (m, 1H), 4.76 (d, J=4.4 Hz, 2H), 4.49-4.45 (m, 1H), 4.36 (d, J=14.0 Hz, 1H), 4.31-4.26 (m, 1H), 3.88 (d, J=10.8 Hz, 1H), 3.80 (d, J=13.2 Hz, 1H), 3.68 (d, J=14.0 Hz, 1H), 3.15-3.09 (m, 1H), 2.94 (dd, J=12.8, 8.6 Hz, 1H), 2.73-2.62 (m, 3H), 2.42-2.31 (m, 2H), 1.11 (d, J=6.2 Hz, 3H); LC-MS(ES$^+$): 572 (M+H)$^+$ (5) Synthesis of Examples 5 to 10

By using procedures identical or analogous to the procedures to prepare the compounds of Examples 1, 2, 3 and to 4, the compounds of Examples 5 to 10 in Table 2 below were prepared from appropriate starting materials which are available or may be prepared by methods known in the art. The compounds were purified using methods well known to those skilled in the art, which may include silica gel chromatography, HPLC, or recrystallization. The final compounds could be isolated as neutrals or as acid addition or base addition salts. The names, NMR data, and LC-MS data of the compounds of the Examples 5-10 are shown in Table 2 below.

TABLE 2

| Example No. | Intermediate A No. | Intermediate B No. | Compound name | NMR data | LC-MS data (ES+) |
|---|---|---|---|---|---|
| 5 | 4 | 9 | (S)-2-((4-(6-((5-cyanopyridin-2-yl)methoxy)pyridin-2-yl)piperazin-1-yl)methyl)-3-(oxetan-2-ylmethyl)-3H-imidazo[4,5-b]pyridine-5-carboxylic acid | $^1$H NMR (DMSO-$d_6$): δ 8.97 (s, 1H), 8.28 (dd, J = 8.0, 2.4 Hz, 1H), 8.15 (d, J = 8.4 Hz, 1H), 8.00 (d, J = 8.4 Hz, 1H), 7.55 (d, J = 8.4 Hz, 1H), 7.48 (t, J =8.0 Hz, 1H), 6.32 (d, J =8.0 Hz, 1H), 6.18 (d, J =8.0 Hz, 1H), 5.41 (s, 2H), 5.16 (m, 1H), 4.86-4.81 (m, 2H), 4.72-4.68 (m, 1H), 4.49-4.47 (m, 1H), 4.38-4.35 (m, 1H), 4.00-3.89 (m, 2H), 3.35-3.33 (brs, 4H, assumed; partially obscured by water peak), 2.68-2.66 (m, 2H), 2.50-2.47 (m, 3H, assumed; partially obscured by solvent peak). | 541 (M + H)$^+$ |
| 6 | 1 | 9 | 2-(((S)-4-(6-((5-cyanopyridin-2-yl)methoxy)pyridin-2-yl)-2-methylpiperazin-1-yl)methyl)-3-(((S)-oxetan-2-ylmethyl)-3H-imidazo[4,5-b]pyridine-5-carboxylic acid | $^1$H NMR (DMSO-$d_6$): δ 8.97 (s, 1H), 8.27 (dd, J = 8.2, 2.0 Hz, 1H), 8.26 (d, J = 2.4 Hz, 1H), 8.14 (d, J = 8.4 Hz, 1H), 7.99 (d, J = 8.0 Hz, 1H), 7.54 (d, J = 8.4 Hz, 1H), 7.47 (t, J = 8.0 Hz, 1H), 6.32 (d, J = 8.0 Hz, 1H), 6.17 (d, J = 8.0 Hz, 1H), 5.40 (s, 2H), 5.23-5.21 (m, 1H), 4.77-4.76 (m, 2H), 4.50-4.44 (m, 2H), 4.21-4.18 (m, 1H), 3.76-3.63 (m, 3H), 2.88 (m, 1H), 2.68-2.60 (m, 4H), 2.5 (m, 1H), 2.25 (m, 1H), 1.06 (d, J = 6.0 Hz, 3H). | 555 (M + H)$^+$ |
| 7 | 13 | 19 | 1-(oxazol-2-ylmethyl)-2-((4-(6-(pyridin-4-ylmethoxy)pyridin-2-yl)piperazin-1-yl)methyl)-1H-benzo[d]imidazole-6-carboxylic acid | $^1$H NMR (DMSO-$d_6$): δ 12.89 (brs, 1H), 8.51 (d, J = 6.0 Hz, 2H), 8.21 (s, 1H), 8.03 (s, 1H), 7.85-7.83 (m, 1H), 7.70-7.68 (m, 1H), 7.44 (t, J = 8.0 Hz, 1H), 7.35 (d, 7 = 6.0 Hz, 2H), 7.11 (s, 1H), 6.26 (d, J = 8.0 Hz, 1H), 6.13 (d, J = 8.0 Hz, 1H), 5.89 (s, 2H), 5.29 (s, 2H), 3.87 (s, 2H), 3.19-3.13 (m, 4H), 2.39-2.35 (m, 4H). | 526 (M + H)$^+$ |
| 8 | 8 | 18 | (S)-2-(4-(6-(5-chloro-3-fluoropyridin-2-yl)methoxy)pyridin-2-yl)piperidin-1-yl)methyl)-1-(oxetan-2-ylmethyl)-1H-benzo[d]imidazole-6-carboxylic acid | $^1$H NMR (400 MHz, MeOD): δ 8.39 (s, 1H), 8.35 (s, 1H), 8.00 (s, 1H), 7.83-7.81 (m, 1H), 7.70-7.68 (m, 1H), 7.60-7.57 (m, 1H), 6.84-6.82 (m, 1H), 6.67-6.65 (m, 1H), 5.55-5.47 (m, 2H), 5.33-5.27 (m, 1H), 4.78 (m, 1H), 4.75-4.74 (m, 1H), 4.52-4.47 (m, 1H), 4.13-3.99 (m, 2H), 3.15-3.11 (m, 1H), 3.04-3.01 (m, 1H), 2.88-2.80 (m, 1H), 2,70-2.51 (m, 2H), 2.46-2.35 (m, 2H), 1.89-1.82 (m, 4H). | 567 (M + H)$^+$ |
| 9 | 16 | 18 | (S)-2-((4-(6-((5-cyanopyridin-2-yl)methoxy)pyridin-2-yl)piperidin-1-yl)methyl)-1-(oxetan-2-ylmethyl)-1H-benzo[d]imidazole-6-carboxylic acid | 1H NMR (400 MHz, CDCl$_3$): δ 8.89 (s, 1H) 8.33 (s, 1H), 8.16-8.13 (m, 1H), 7.99-7.97 (m, 2H), 7.68-7.61 (m, 3H), 6.87-6.85 (m, 1H), 6.78-6.76 (m, 1H), 5.57 (s, 2H), 5.30-5.28 (m, 1H), 4.72-4.65 (m, 1H), 4.52-4.46 (m, 1H), 4.07-4.04 (m, 1H), 3.96-3.91 (m, 1H), 3.08-3.05 (m, 1H), 2.97-2.94 (m, 1H), 2.86-2.82 (m, 1H), 2.58-2.51 (m, 2H), 2.38-2.28 (m, 2H), 1.82-1.72 (m, 3H). | 539 (M + H)$^+$ |

TABLE 2-continued

| Example No. | Intermediate A No. | Intermediate B No. | Compound name | NMR data | LC-MS data (ES+) |
|---|---|---|---|---|---|
| 10 | 17 | 18 | (S)-2-((4-(3-((5-chloro-3-fluoropyridin-2-yl)methoxy)phenyl)piperidin-1-yl)methyl)-1-(oxetan-2-ylmethyl)-1H-benzo[d]imidazole-6-carboxylic acid | $^1$H NMR (400 MHz, DMSO-$d_6$): δ 8.56 (d, J = 1.3 Hz, 1H), 8.28-8.26 (m, 1H), 8.18 (dd, J = 9.7, 1.9 Hz, 1H), 7.83-7.79 (m, 1H), 7.65-7.61 (m, 1H), 7.24-7.18 (m, 1H), 6.90-6.84 (m, 3H), 5.21-5.19 (m, 2H), 5.16-5.06 (m, 1H), 4.81 (dd, J = 15.3, 7.3 Hz, 1H), 4.67 (dd, J = 15.2, 2.6 Hz, 1H), 4.54-4.47 (m, 1H), 4.42-4.34 (m, 1H), 3.95 (d, J = 13.5 Hz, 1H), 3.82-3.76 (m, 1H), 3.00 (d, J = 11.0 Hz, 1H), 2.87 (t, J = 7.6 Hz, 1H), 2.78-2.67 (m, 1H), 2.47-2.39 (m, 1H), 2.28-2.12 (m, 2H), 1.76-1.74 (m, 4H). | 566 (M + H)+ |

2. Preparation Example B

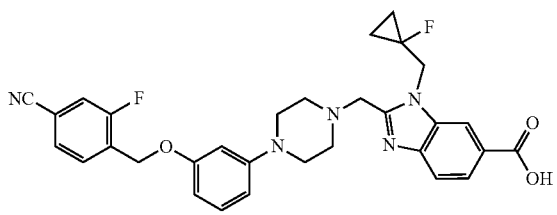 [SMILES: N#Cc1ccc(COc2cccc(N3CCN(Cc4nc5ccc(C(=O)O)cc5n4CC4(F)CC4)CC3)c2)c(F)c1]

(1) Synthesis of Example 11: 2-((4-(3-((4-cyano-2-fluorobenzyl)oxy)phenyl)piperazin-1-yl)methyl)-1-((1-fluorocyclopropyl)methyl)-1H-benzo[d]imidazole-6-carboxylic acid 1) Synthesis of methyl 2-((4-(3-((4-cyano-2-fluorobenzyl)oxy)phenyl)piperazin-1-yl)methyl)-1-((1-fluorocyclopropyl)methyl)-1H-benzo[d]imidazole-6-carboxylate Intermediate 3 (0.3 mmol), intermediate 10 (89 mg), and potassium carbonate (124 mg, 0.9 mmol) were dissolved in CH$_3$CN (3.0 mL) in a round bottom flask, and the mixture was stirred at 80° C. or 4 hours. The mixture was cooled to room temperature and filtered through a celite pad to obtain a filtrate. The filtrate was concentrated under reduced pressure. The residue was purified by silica gel column chromatography with a hexane/ethyl to obtain methyl 2-((4-(3-((4-cyano-2-fluorobenzyl)oxy)phenyl)piperazin-1-yl)methyl)-1-((1-fluorocyclopropyl)methyl)-1H-benzo[d]imidazole-6-carboxylate (93 mg, 57%) as a white solid. LC-MS(ES+): 572 (M+H)+

2) Synthesis of the Final Compound

The compound (60 mg) obtained in the step 1) was dissolved in 1,4-dioxane/water (4:1, 2.5 mL). After 1 N NaOH aqueous solution (0.2 mL) was added dropwise, the mixture was stirred at room temperature for 24 hours. The mixture was neutralized with 1 N HCl aqueous solution. Then, the mixture was extracted with DCM/MeOH 5% solution. The resulting organic layer was dried over anhydrous magnesium sulfate, filtered, and concentrated under reduced pressure. The residue was purified by silica gel column chromatography with DCM/MeOH (12 g SiO$_2$, 5% methanol in DCM→10% methanol in DCM) to obtain the final compound (25 mg, 46%) as a white solid. $^1$H NMR (400 MHz, DMSO-$d_6$) δ 12.82 (m, 1H), 8.29 (s, 1H), 7.91 (d, J=10.4 Hz, 1H), 7.83-7.80 (m, 1H), 7.77-7.73 (m, 2H), 7.70-7.64 (m, 1H), 7.14-7.09 (m, 1H), 6.57-6.55 (m, 2H), 6.47-6.45 (m, 1H), 5.20 (s, 2H), 4.99 (d, J=22.0 Hz, 2H), 3.87 (s, 2H), 3.13 (m, 4H), 2.60 (s, 4H), 1.07-1.02 (m, 4H); LC-MS(ES+): 556 (M+H)+

(2) Synthesis of Examples 12 to 17

By using procedures identical or analogous to the procedure to prepare the compound of Example 11, the compounds of Examples 12 to 17 in Table 3 below were prepared from appropriate starting materials which are available commercially or may be prepared by methods known in the art. The compounds were purified using methods well known to those skilled in the art, which may include silica gel chromatography, HPLC, or recrystallization. The final compounds could be isolated as neutrals or as acid addition or base addition salts. The names, NMR data, and LC-MS data of the compounds of Examples 12-17 are shown in Table 3 below.

TABLE 3

| Example No. | Intermediate A No. | Intermediate B No. | Compound name | NMR data | LC-MS data (ES+) |
|---|---|---|---|---|---|
| 12 | 11 | 18 | (S)-2-((4-(6-(5-cyanopyridin-2-yl)methoxy)pyrazin-2-yl)piperazin-1-yl)methyl)-1-(oxetan-2-ylmethyl)-1H-benzo[d]imidazole-6-carboxylic acid | $^1$H NMR (400 MHz, CDCl$_3$): δ 8.84 (s, 1H), 8.21 (s, 1H), 8.05 (dd, J = 8.4, 1.2 Hz, 1H), 7.96 (dd, J = 8.0, 2.0 Hz, 1H), 7.81 (d, J = 8.8 Hz, 1H), 7.68 (d, 7 = 3.6 Hz, 2H), 7.57 (d, J = 8.0 Hz, 1H), 5.48 (s, 2H), 5.30 (s, 2H), 5.24-5.22 (m, 1H), 4.71-4.62 (m, 3H), 4.39-4.36 (m, 1H), 4.10-3.95 (m, 3H), 3.48 (s, 4H), 2.79-2.68 (m, 1H), 2.63 (s, 4H), 2.47-2.44 (m, 1H), 2.04 (s, 3H), 1.31-1.23 (m, 3H), 0.89-0.85 (m, 1H). | 541 (M + H)+ |

TABLE 3-continued

| Example No. | Intermediate A No. | Intermediate B No. | Compound name | NMR data | LC-MS data (ES+) |
|---|---|---|---|---|---|
| 13 | 12 | 9 | (S)-2-((4-(3-(5-cyanopyridin-2-yl)methoxy)phenyl)piperazin-1-yl)methyl)-3-(oxetane-2-yl-methyl)-3H-imidazo[4,5-b]pyridine-5-carboxylic acid | $^{1}$H NMR (400 MHz, DMSO-$d_6$): δ 9.04 (brs, 1H), 8.35 (dd, J = 8.2, 2.2 Hz, 1H), 8.03 (d, J = 8.0Hz, 1H), 7.96 (d, J = 8.0 Hz, 1H), 7.70 (d, J = 8.4 Hz, 1H), 7.11 (t, J = 8.2 Hz, 1H), 6.58-6.54 (m, 2H), 6.44 (dd, J = 8.0, 2.0 Hz, 1H), 5.25 (s, 2H), 5.19-5.17 (m, 1H), 4.78 (brs, 2H), 4.48-4.45 (m, 1H), 4.28-4.25 (m, 1H), 3.94 (q, J = 14.0 Hz, 2H), 3.13 (s, 4H), 2.65-2.60 (m, 5H), 2.51-2.45 (m, 1H). | 540 (M + H)$^+$ |
| 14 | 12 | 18 | (S)-2-((4-(3-(5-cyanopyridin-2-yl)methoxy)phenyl)piperazin-1-yl)methyl)-1-(oxetane-2-ylmethyl)-1H-benzo[d]imidazole-6-carboxylic acid | $^{1}$H NMR (400 MHz, DMSO-$d_6$): δ 12.83 (bs, 1H), 9.04 (dd, J = 2.0, 0.8 Hz, 1H), 8.36 (dd, J = 6.0, 1.6 Hz, 1H), 8.28 (d, J = 1.2 Hz, 1H), 7.81 (dd, J = 8.4, 1.6 Hz, 1H), 7.67 (dd, J = 18.0, 8.0 Hz, 2H), 7.11 (t, J =8.0 Hz, 1H), 6.58-6.54 (m, 2H), 6.43 (dd, J = 8.0, 2.0 Hz, 1H), 5.25 (s, 1H), 5.12-5.07 (m, 1H), 4.79 (dd, J = 15.2, 7.4 Hz, 1H), 4.65 (dd, J = 15.2, 2.6 Hz, 1H), 4.51-4.46 (m, 1H), 4.41-4.35 (m, 1H), 4.00 (d, J = 13.5 Hz, 1H), 3.81 (d, J = 13.5 Hz, 1H), 3.13-3.12 (m, 1H), 2.74-2.67 (m, 1H), 2,65-2.56 (m, 4H), 2.46-2.35 (m, 2H), 2.47-2.41 (m, 1H), 1.89-1.82 (m, 4H). | 539 (M + H)$^+$ |
| 15 | 14 | 19 | 1-(oxazol-2-ylmethyl)-2-((4-(6-(pyridin-2-ylmethoxy)pyridin-2-yl)piperazin-1-yl)methyl)-1H-benzo[d]imidazole-6-carboxylic acid | $^{1}$H NMR (400 MHz, CDCl$_3$): δ 8.60 (d, J = 4.0 Hz, 1H), 8.29 (s, 1H), 8.05 (d, J = 8.0 Hz, 1H), 7.80 (d, J = 8.0 Hz, 1H), 7.69 (t, J = 8.0 Hz, 1H), 7.57 (s, 1H), 7.47 (d, J = 8.0 Hz, 1H), 7.41 (t, J = 8.0 Hz, 1H), 7.22-7.19 (m, 1H), 7.08 (s, 1H), 6.21 (d, J = 8.0 Hz, 1H), 6.13 (d, J = 8.0 Hz, 1H), 5.81 (s, 2H), 5.48 (s, 2H), 3.99 (s, 2H), 3.49 (s, 1H), 3.37 (s, 4H), 2.59 (s, 4H). | 526 (M + H)$^+$ |
| 16 | 6 | 18 | (S)-2-((4-(6-((5-chloro-3-fluoropyridin-2-yl)methoxy)pyridin-2-yl)piperazin-1-yl)methyl)-1-(oxetan-2-ylmethyl)-1H-benzo[d]imidazole-6-carboxylic acid | $^{1}$H NMR (400 MHz, DMSO-$d_6$) δ 8.50 (d, J = 1.2 Hz, 1H), 8.28 (s, 1H), 8.10 (dd, J = 9.8, 1.8 Hz, 1H), 7.82 (dd, 7 = 8.4, 1.2 Hz, 1H), 7.65 (d, 7 = 8.4 Hz, 1H), 7.45 (t, 7 = 8.0 Hz, 1H), 6.32 (d, 7= 8.0 Hz, 1H), 6.09 (d, 7 = 7.6 Hz, 1H), 5.38 (d,7 = 1.6 Hz, 2H), 5.11 (dd, 7 = 7.2, 2.4 Hz, 1H), 4.80 (dd, 7 = 15.4, 7.4 Hz, 1H), 4.65 (dd, 7 = 15.0, 2.6 Hz, 1H), 4.51-4.46 (m, 1H), 4.41-4.37 (m, 1H), 3.97 (d, 7 = 13.2 Hz, 1H), 3.80 (d, 7 = 13.6 Hz, 1H), 3.41 (t, 7 = 4.6 Hz, 4H), 2.74-2.68 (m, 1H), 2.56-2.48 (m, 4H), 2.46-2.43 (m, 1H). | 567 (M + H)$^+$ |
| 17 | 15 | 18 | (S)-2-((4-(6-(5-chloropyridin-2-yl)methoxy)pyridin-2-yl)piperazin-1-yl)methyl)-1-(oxetan-2-ylmethyl)-1H-benzo[d]imidazole-6-carboxylic acid | $^{1}$H NMR (400 MHz, DMSO-$d_6$): δ 12.78 (brs, 1H), 8.58 (dd, J = 2.5 Hz, 1H), 8.27 (d, J = 1.0 Hz, 1H), 7.91 (dd, 7 = 8.4, 2.5 Hz, 1H), 7.81 (dd, 7 = 8.4, 1.5 Hz, 1H), 7.65 (d, 7 = 8.4 Hz , 1H), 7.50-7.43 (m, 2H), 6.32 (d, 7 = 8.1 Hz, 1H), 6.15 (d, 7 = 7.8 Hz, 1H), 5.34 (s, 2H), 5.11-5.08 (m, 1H), 4.79 (dd, 7 = 15.3, 7.4 Hz, 1H), 4.65 (dd, 7 = 15.2, 2.5 Hz, 1H), 4.51-4.46 (m, 1H), 4.0-4.35 (m, 1H), 3.96 (d, 7 = 13.6 Hz, 1H), 3.78 (d, 7 = 13.6 Hz, 1H), 3.41-3.36 (m, 4H), 2.74-2.66 (m, 1H), 2.48-2.38 (m, 4H). | 549 (M + H)$^+$ |

3. Preparation Example C

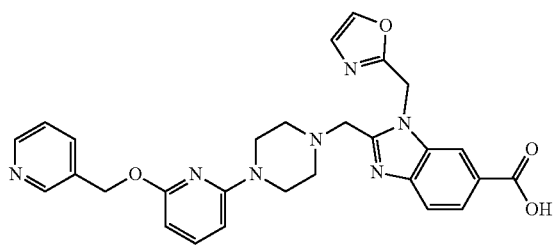 [SMILES: O=C(O)c1ccc2nc(CN3CCN(c4cccc(OCc5cccnc5)n4)CC3)n(Cc3ncco3)c2c1]

(1) Synthesis of Example 18: 1-(oxazol-2-ylmethyl)-2-((4-(6-(pyridin-3-ylmethoxy)pyridin-2-yl)piperazin-1-yl)methyl)-1H-benzo[d]imidazole-6-carboxylic acid 1) Synthesis of methyl 1-(oxazol-2-ylmethyl)-2-((4-(6-(pyridin-3-ylmethoxy)pyridin-2-yl)piperazin-1-yl)methyl)-1H-benzo[d]imidazole-6-carboxylate Intermediate 5 (130 mg), intermediate 19 (147 mg), and potassium carbonate (332 mg) were dissolved in CH$_3$CN (1.5 mL) in a round bottom flask, and the mixture was stirred at 50° C. for 4 hours. After purified water was added, the mixture was cooled to room temperature and stirred at the same temperature for 2 hours. The resulting solid was filtered, washed with purified water: CH$_3$CN (2:1), and was dried to obtain methyl 1-(oxazol-2-ylmethyl)-2-((4-(6-(pyridin-3-ylmethoxy)pyridin-2-yl)piperazin-1-yl)methyl)-1H-benzo[d]imidazole-6-carboxylate (52 mg, 20%). LC-MS (ES⁺): 540 (M+H)⁺

2) Synthesis of the Final Compound

The compound (45 mg) obtained in the step 1) was dissolved in 1,2-dichloroethane (3.0 mL). After Me₃SnOH (49 mg) was added, the mixture was stirred at 80° C. for 6 days. The mixture was concentrated and extracted with EA. The resulting organic layer was washed with aqueous hydrochloric acid solution, dried over anhydrous magnesium sulfate, filtered, and concentrated under reduced pressure. The residue was purified by silica gel column chromatography with DCM/MeOH/AcOH to obtain the final compound (8 mg, 18%) as a brown solid. ¹H NMR (400 MHz, MeOD): δ 8.60 (d, J=1.8 Hz, 1H), 8.46 (dd, J=4.8, 0.8 Hz, 1H), 8.27 (s, 1H), 8.03 (d, J=8.8 Hz, 1H), 7.91-7.89 (m, 2H), 7.72 (d, J=8.4 Hz, 1H), 7.46-7.42 (m, 2H), 7.14 (s, 1H), 6.25 (d, J=8.0 Hz, 1H), 6.14 (d, J=7.6 Hz, 1H), 5.38 (s, 2H), 3.98 (s, 2H), 3.37-3.34 (m, 4H), 2.55 (t, J=4.8 Hz, 4H); LC-MS (ES⁺): 526 (M+H)⁺

The chemical structures and names of the compounds of Examples 1 to 18 prepared using the Preparation Examples A, B and C are shown in Table 4 below.

TABLE 4

| Examples | Structure | Compound names |
|---|---|---|
| 1 | 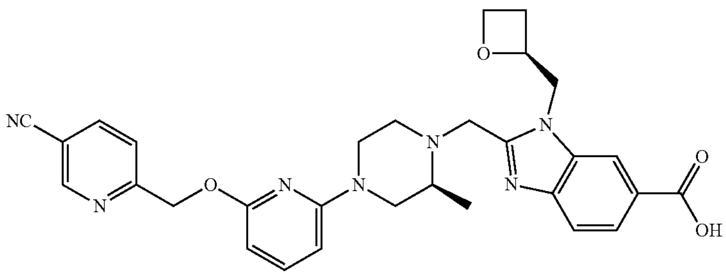 [SMILES: C[C@H]1CN(c2cccc(OCc3ccc(C#N)cn3)n2)CCN1Cc1nc2ccc(C(=O)O)cc2n1C[C@@H]1CCO1] | 2-(((S)-4-(6-((5-cyanopyridin-2-yl)methoxy)pyridin-2-yl)-2-methylpiperazin-1-yl)methyl)-1-(((S)-oxetan-2-yl)methyl)-1H-benzo[d]imidazole-6-carboxylic acid |
| 2 | 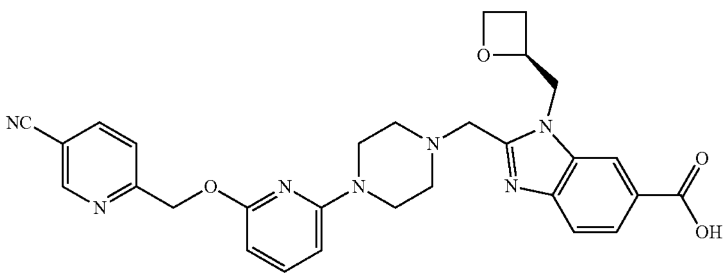 [SMILES: N#Cc1ccc(COc2cccc(N3CCN(Cc4nc5ccc(C(=O)O)cc5n4C[C@@H]4CCO4)CC3)n2)nc1] | (S)-2-((4-(6-((5-cyanopyridin-2-yl)methoxy)pyridin-2-yl)piperazin-1-yl)methyl)-1-(oxetan-2-ylmethyl)-1H-benzo[d]imidazole-6-carboxylic acid |
| 3 | 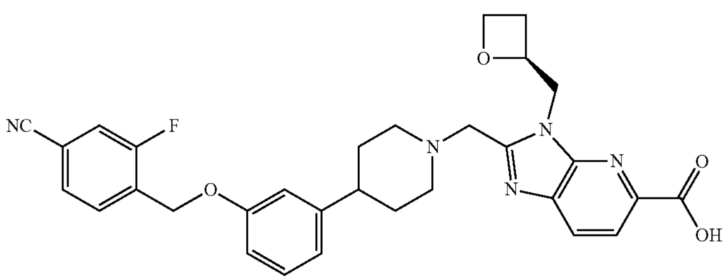 [SMILES: N#Cc1ccc(COc2cccc(C3CCN(Cc4nc5ccc(C(=O)O)nc5n4C[C@@H]4CCO4)CC3)c2)c(F)c1] | (S)-2-((4-(3-((4-cyano-2-fluorobenzyl)oxy)phenyl)piperidin-1-yl)methyl)-3-(oxetan-2-yl-methyl)-3H-imidazo[4,5-b]pyridine-5-carboxylic acid |
| 4 | 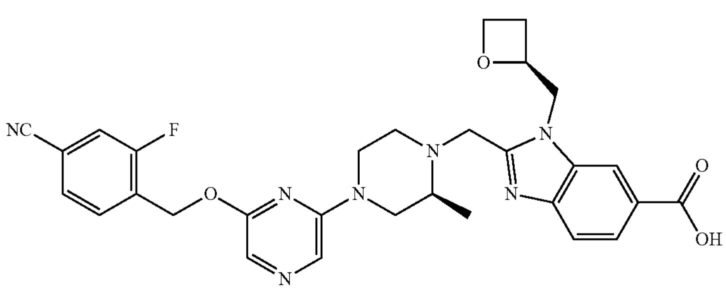 [SMILES: C[C@H]1CN(c2cncc(OCc3ccc(C#N)cc3F)n2)CCN1Cc1nc2ccc(C(=O)O)cc2n1C[C@@H]1CCO1] | 2-(((S)-4-(6-((4-cyano-2-fluorobenzyl)oxy)pyrazin-2-yl)-2-methylpiperazin-1-yl)methyl)-1-(((S)-oxetan-2-yl)methyl)-1H-benzo[d]imidazole-6-carboxylic acid |

TABLE 4-continued

| Examples | Structure | Compound names |
|---|---|---|
| 5 | 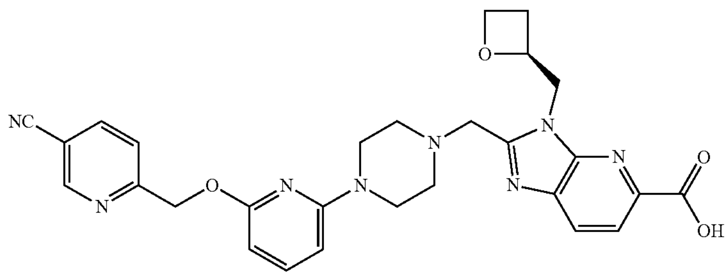 [SMILES: N#Cc1ccc(COc2cccc(N3CCN(Cc4nc5ccc(C(=O)O)nc5n4C[C@@H]4CCO4)CC3)n2)nc1] | (S)-2-((4-(6-((5-cyanopyridin-2-yl)methoxy)pyridin-2-yl)piperazin-1-yl)methyl)-3-(oxetane-2-ylmethyl)-3H-imidazo[4,5-b]pyridine-5-carboxylic acid |
| 6 | 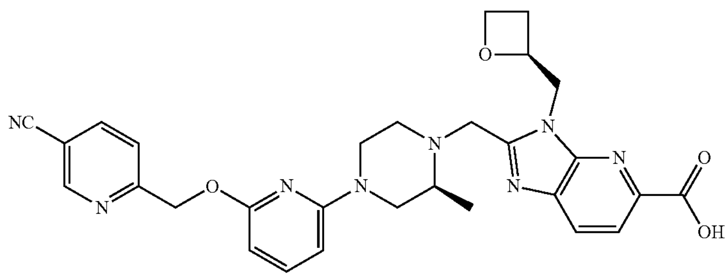 [SMILES: C[C@H]1CN(c2cccc(OCc3ccc(C#N)cn3)n2)CCN1Cc1nc2ccc(C(=O)O)nc2n1C[C@@H]1CCO1] | 2-(((S)-4-(6-((5-cyanopyridin-2-yl)methoxy)pyridin-2-yl)-2-methylpiperazin-1-yl)methyl)-3-(((S)-oxetan-2-yl)methyl)-3H-imidazo[4,5-b]pyridine-5-carboxylic acid |
| 7 | 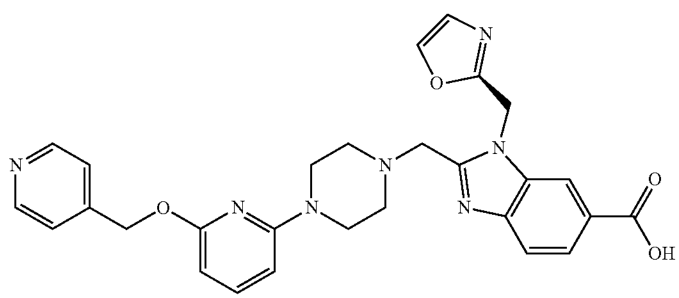 | 1-(oxazol-2-ylmethyl)-2-((4-(6-(pyridin-4-ylmethoxy)pyridin-2-yl)piperazin-1-yl)methyl)-1H-benzo[d]imidazole-6-carboxylic acid |
| 8 | 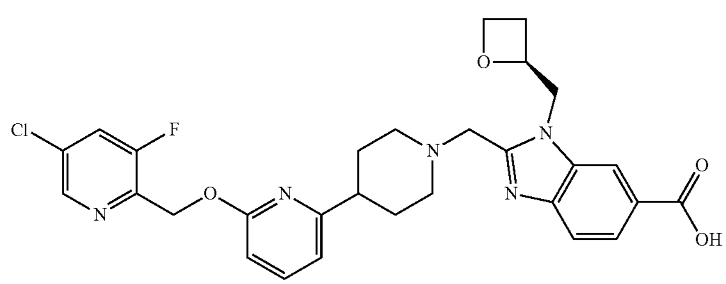 [SMILES: O=C(O)c1ccc2nc(CN3CCC(c4cccc(OCc5ncc(Cl)cc5F)n4)CC3)n(C[C@@H]3CCO3)c2c1] | (S)-2-((4-(6-((5-chloro-3-fluoropyridin-2-yl)methoxy)pyridin-2-yl)piperidin-1-yl)methyl)-1-(oxetan-2-ylmethyl)-1H-benzo[d]imidazole-6-carboxylic acid |
| 9 | 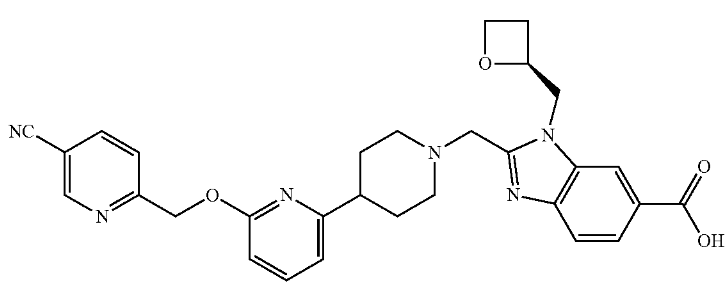 [SMILES: N#Cc1ccc(COc2cccc(C3CCN(Cc4nc5ccc(C(=O)O)cc5n4C[C@@H]4CCO4)CC3)n2)nc1] | (S)-2-((4-(6-((5-cyanopyridin-2-yl)methoxy)pyridin-2-yl)piperidin-1-yl)methyl)-1-(oxetane-2-ylmethyl)-1H-benzo[d]imidazole-6-carboxylic acid |

TABLE 4-continued

| Examples | Structure | Compound names |
| --- | --- | --- |
| 10 | 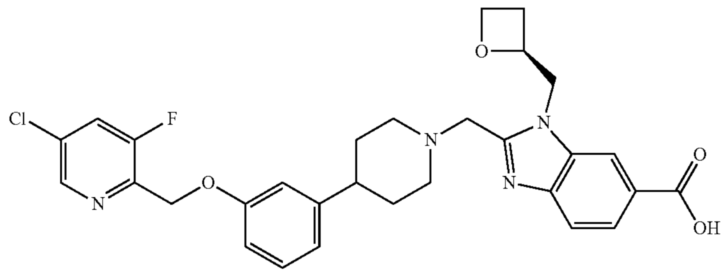 [SMILES: O=C(O)c1ccc2nc(CN3CCC(c4cccc(OCc5ncc(Cl)cc5F)c4)CC3)n(C[C@@H]3CCO3)c2c1] | (S)-2-((4-(3-((5-chloro-3-fluoropyridin-2-yl)methoxy)phenyl)piperidin-1-yl)methyl)-1-(oxetane-2-ylmethyl)-1H-benzo[d]imidazole-6-carboxylic acid |
| 11 | 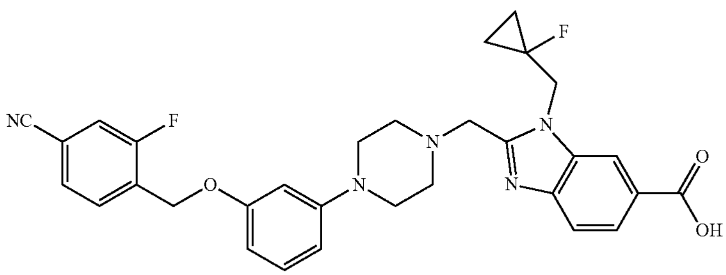 [SMILES: N#Cc1ccc(COc2cccc(N3CCN(Cc4nc5ccc(C(=O)O)cc5n4CC4(F)CC4)CC3)c2)c(F)c1] | 2-((4-(3-((4-cyano-2-fluorobenzyl)oxy)phenyl)piperazin-1-yl)methyl)-1-((1-fluorocyclopropyl)methyl)-1H-benzo[d]imidazole-6-carboxylic acid |
| 12 | 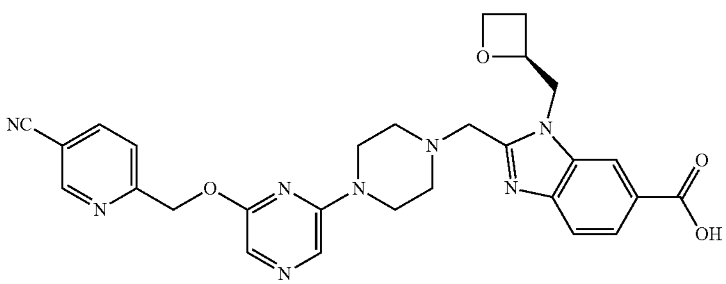 [SMILES: N#Cc1ccc(COc2cncc(N3CCN(Cc4nc5ccc(C(=O)O)cc5n4C[C@@H]4CCO4)CC3)n2)nc1] | (S)-2-((4-(6-((5-cyanopyridin-2-yl)methoxy)pyrazin-2-yl)piperazin-1-yl)methyl)-1-(oxetane-2-ylmethyl)-1H-benzo[d]imidazole-6-carboxylic acid |
| 13 | 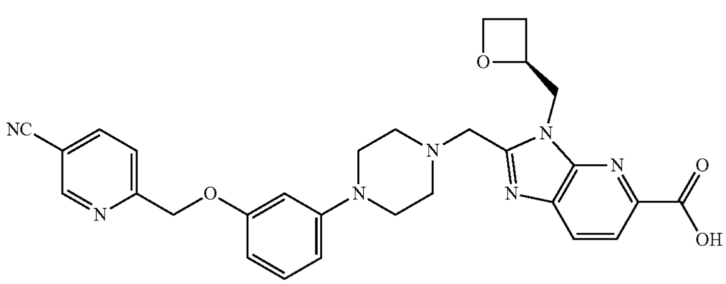 [SMILES: N#Cc1ccc(COc2cccc(N3CCN(Cc4nc5ccc(C(=O)O)nc5n4C[C@@H]4CCO4)CC3)c2)nc1] | (S)-2-((4-(3-((5-cyanopyridin-2-yl)methoxy)phenyl)piperazin-1-yl)methyl)-3-(oxetan-2-ylmethyl)-3H-imidazo[4,5-b]pyridine-5-carboxylic acid |
| 14 | 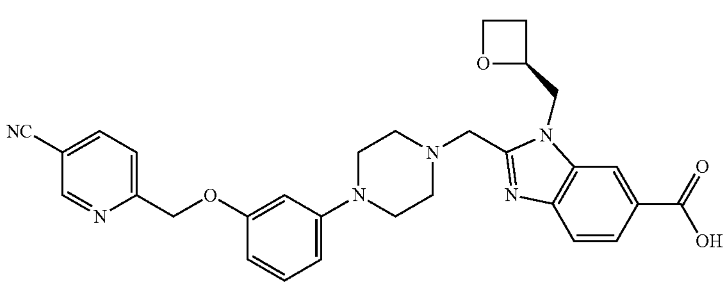 [SMILES: N#Cc1ccc(COc2cccc(N3CCN(Cc4nc5ccc(C(=O)O)cc5n4C[C@@H]4CCO4)CC3)c2)nc1] | (S)-2-((4-(3-((5-cyanopyridin-2-yl)methoxy)phenyl)piperazin-1-yl)methyl)-1-(oxetan-2-ylmethyl)-1H-benzo[d]imidazole-6-carboxylic acid |

TABLE 4-continued

| Examples | Structure | Compound names |
|---|---|---|
| 15 | 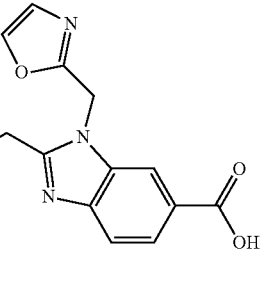 | 1-(oxazol-2-ylmethyl)-2-((4-(6-(pyridin-2-ylmethoxy)pyridin-2-yl)piperazin-1-yl)methyl)-1H-benzo[d]imidazole-6-carboxylic acid |
| 16 | 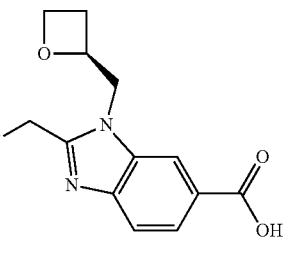 | (S)-2-((4-(6-((5-chloro-3-fluoropyridin-2-yl)methoxy)pyridin-2-yl)piperazin-1-yl)methyl)-1-(oxetan-2-ylmethyl)-1H-benzo[d]imidazole-6-carboxylic acid |
| 17 | 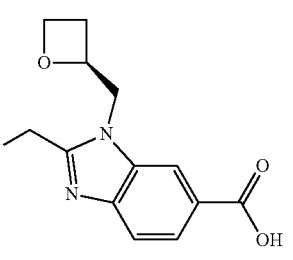 | (S)-2-((4-(6-((5-chloropyridin-2-yl)methoxy)pyridin-2-yl)piperazin-1-yl)methyl)-1-(oxetane-2-ylmethyl)-1H-benzo[d]imidazole-6-carboxylic acid |
| 18 | 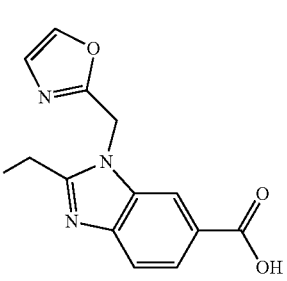 | 1-(oxazol-2-ylmethyl)-2-((4-(6-(pyridin-3-ylmethoxy)pyridin-2-yl)piperazin-1-yl)methyl)-1H-benzo[d]imidazole-6-carboxylic acid |

EXPERIMENTAL EXAMPLES

1. Experimental Example 1: cAMP Assay

A cAMP assay test was performed according to a method optimized based on a protocol provided by a cAMP assay kit manufacturer (CISBIO). GLP-1 receptor CHO-K1 cells were dispensed into 96-well plates for cAMP measurement (low volume, white) at $6 \times 10^3$ cells/well/5 mL. As a control substance, 5 mL of Exendin-4 at the concentration of 0, 1, 10, 100, 1000, and 10000 pM was treated to each of the wells of one of the plates. 5 mL of the compounds according to the Examples 1, 2, 3, 4, 5, 10, 11, 13, 14, 16 and 17 at the concentration of 0, 1, 10, 100, 1000, 10000 nM was treated to each of the wells of the other plates, respectively. The cells were incubated at room temperature for 7 minutes. A cAMP-$d_2$ conjugate reagent was prepared by mixing a cAMP conjugate with an elution buffer at a ratio of 1:4. An anti-cAMP cryptate conjugate reagent was prepared by mixing a cGMP conjugate with an elution buffer at a ratio of 1:4. Then, 5 mL of the cAMP-$d_2$ conjugate reagent was added to each of the wells. Subsequently, 5 mL of the anti-cAMP cryptate conjugate reagent was added to each of the wells. After incubation of the cells at room temperature for 1 hour, HTRF signals at wavelengths of 665 nm and 620 nm of the culture were measured using a FlexStaton 3 (Molecular Devices) instrument. The ratio of 665/620 was calculated from the measured values at 665 nm and 620 nm with regard to Exendin-4 and the compounds of the Examples, respectively. By converting the ratio with regard to Exendin-4 to 100%, Emax values of the compounds of the Examples were calculated as the cAMP stimulation ratio of the compounds. The results are shown in Table 5 below. In the table, ++ means that $EC_{50}$ is smaller than 50 nM, and + means that $EC_{50}$ is 50~100 nM.

TABLE 5

| Example No. | $EC_{50}$ (nM) | $E_{max}$ (%) |
|---|---|---|
| 1 | ++ | 103.79 |
| 2 | ++ | 107.81 |
| 3 | ++ | 108.19 |
| 4 | ++ | 108.76 |
| 5 | + | 110.68 |
| 10 | + | 96.41 |
| 11 | ++ | 96.45 |
| 13 | ++ | 128.05 |
| 14 | ++ | 91.37 |
| 16 | ++ | 101.90 |
| 17 | ++ | 100.52 |

2. Experimental Example 2: Analysis of Intravenous Glucose Tolerance Via Intravenous Administration (1) Sample Preparation Before the intravenous glucose tolerance test (ivGTT) was performed, monkeys to be used in the test were fasted for 16 hours. After the fasting, fasting blood sugar was measured on the day of the test, and the monkeys were grouped to minimize blood sugar deviation. Each of the monkeys was fixed on a correction chair and anesthetized. A tube catheter was inserted into a saphenous vein of the monkey immediately before glucose administration (0 minute), and the test substance (1 mg/mL/kg) was administered intravenously. After the drug administration, glucose (0.25 g/kg, 50% dextrose solution 0.5 mL/kg) was intravenously administered through the tube catheter inserted into the vein. Blood was collected from the femoral vein immediately before the glucose administration (0 minute) and on 15, 30, 40, 50, 60, and 120 minutes after the glucose administration, and then plasma was separated via centrifugation within 30 minutes after the blood collection. The separated plasma samples were stored in a frozen state until insulin analysis.

(2) Insulin Analysis Method

The frozen plasma samples were slowly thawed on ice. An ELISA test was performed according to a protocol provided with a Monkey insulin ELISA kit (LSBio, Cat No. LS-F10306). An insulin concentration was calculated by drawing a standard curve using the absorbance of the insulin standard and applying the absorbance of each measured sample thereto. The analysis results with regard to the compounds of some of the Examples are shown in Table 6 below. In the table, ++ means that a maximum insulin concentration is greater than 250 IU/mL, and + means that a maximum insulin concentration is 200~250 IU/mL.

TABLE 6

| Example No. | Monkey ivGTT (iv) $insulin_{max}$ (IU/mL) |
|---|---|
| 1 | ++ |
| 3 | ++ |
| 4 | ++ |
| 6 | ++ |
| 13 | + |
| 14 | + |
| 17 | + |

The result of the intravenous glucose tolerance analysis shows that the compounds according to the present disclosure exhibited insulin secretion efficacy.

3. Experimental Example 3: Analysis of Intravenous Glucose Tolerance Via Oral Administration (1) Preparation for Experiment Before performing the ivGTT, the monkeys to be used in the test were fasted for 16 hours. After the fasting, fasting blood sugar was measured on the day of the test, and then the monkeys were grouped to minimize blood sugar deviation. On 60 minutes before glucose administration (-60 minutes), each of the monkeys was fixed on a correction chair, and the test substance (50 mg/5 mL/kg) was administered orally using a catheter for oral administration. The monkey fixed on the correction chair was anesthetized, and glucose (0.25 g/kg, 50% dextrose solution 0.5 mL/kg) was intravenously administered through a tube catheter inserted into the vein. Blood was collected from the femoral vein immediately before the glucose administration (0 minute) and on 15, 30, 40, 50, 60, and 120 minutes after the glucose administration, and plasma was separated via centrifugation within 30 minutes after the blood collection. The separated plasma samples were stored in a frozen state until insulin analysis.

(2) Insulin Analysis Method

The frozen plasma samples were slowly thawed on ice. An ELISA test was performed according to a protocol provided with a Monkey insulin ELISA kit (LSBio, Cat No. LS-F10306). An insulin concentration was calculated by drawing a standard curve using the absorbance of the insulin standard and applying the absorbance of each measured sample thereto. The analysis results with regard to the compounds of some of the Examples are shown in Table 7 below. In the table, ++ means that a maximum insulin concentration is greater than 100 IU/mL, and + means that a maximum insulin concentration is 50~100 IU/mL.

TABLE 7

| Example No. | Monkey ivGTT (po) $insulin_{max}$ (IU/mL) |
|---|---|
| 1 | + |
| 2 | ++ |
| 3 | ++ |
| 4 | ++ |
| 6 | + |
| 11 | ++ |

The compounds according to the present disclosure exhibited excellent insulin secretion efficacy also in the oral administration mode.

4. Experimental Example 4: hERG Analysis

The inhibition of activity of hERG (human ether-a-go-go related gene) potassium channel by the compounds was evaluated by using an automatic whole-cell patch clamp system (QPatch 48 HT, Sophion Bioscience) that can directly measure the flow of ions through the potassium channel in cells. A CHO-K1 cell line stably expressing human hERG cDNA (Kv11.1, KCNH2) was used. The composition of the intracellular solution (mM) used for the analysis is 70 KF, 60 KCl, 15 NaCl, 5 HEPES, 5 EGTA, 5 MgATP, pH 7.3 by KOH. The composition of the extracellular solution (mM) used for the analysis is 137 NaCl, 4 KCl, 1 $MgCl_2$, 1.8 $CaCl_2$), 10 HEPES, 10 glucose, pH 7.35 by NaOH.

The hERG-expressing CHO-K1 cell line was treated with each compound at five concentrations (1, 3, 10, 30 and 100 μM), and incubated with each test concentration for 5 minutes in duplicate. All experiments were conducted at room temperature. Change in current amplitude through the hERG channel was recorded every 8 seconds.

Stock solution for each compound is prepared in DMSO at 300× the final assay concentrations, and stored at −20° C. until the day of assay. On the day of the experiment, the stock was diluted into an extracellular solution to make final treatment concentration. To ensure the validity of the test system, a positive control substance E-4031 (0.003 to 0.3 μM) was used for each test. A final concentration of 0.33% DMSO is maintained for each concentration of the assay compounds and controls.

The change in hERG current before and after treatment with the test substance was recorded using the automatic whole cell patch clamp, and the hERG inhibition percentage (%) was calculated based on the control group.

$IC_{50}$ (the concentration of the compound at which 50% of channel inhibition was observed) was calculated using GraphPad Prism based on an average value of the hERG inhibition percentages (%) based on concentrations of each substance. In this calculation, an inhibitor dose-response curve analyzed by using a curve fitting program that uses a 4-parameter logistic dose response equation was used. Thus, a potential risk of QT prolongation depending on the dose of each substance was predicted. The analysis results with regard to the compounds of some of the Examples are shown in following Table 8. Example 4A-01 described in WO2018109607 of Pfizer was used as a control substance.

TABLE 8

| Example No. | $IC_{50}$ (μM) |
|---|---|
| Control substance | 4.3 |
| 1 | >100 |
| 2 | >100 |
| 3 | 34.6 |
| 4 | 55.8 |
| 6 | >100 |
| 11 | 18.5 |
| 13 | >100 |
| 14 | >100 |
| 16 | >100 |
| 17 | >100 |

The result of the experiment that the hERG inhibition percentage of the compounds according to the present disclosure is lower than that of the control substance shows that the safety of the compounds according to the present disclosure is improved.

The invention claimed is:

1. A compound represented by a following Chemical Formula 1, an optical isomer of the compound, or a pharmaceutically acceptable salt of the compound or the optical isomer:

[Chemical Formula 1]

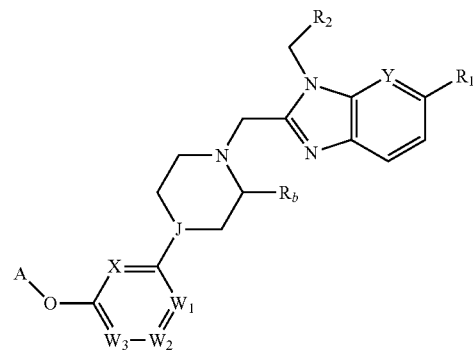

wherein:
$R_1$ is —C(=O)$R_a$, where $R_a$ is —OH;
Y is —CH— or —N—;
$R_2$ is unsubstituted

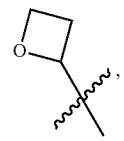

halogen substituted

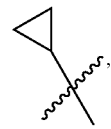 [SMILES: *C1CC1]

or unsubstituted

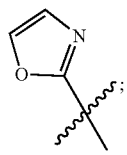

$R_b$ is hydrogen or —($C_1$-$C_4$ alkyl);
J is —N—;
X is —$CR_c$— or —N—, where $R_c$ is —H;
$W_1$ is —$CR_d$—, where $R_d$ is —H;
$W_2$ is —$CR_e$— or —N—, where $R_e$ is —H;
$W_3$ is —$CR_f$—, where $R_f$ is —H; and
A is

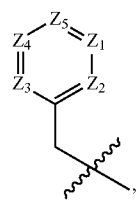

wherein $Z_1$ is —$CR_g$—, where $R_g$ is —H, halogen or —CN;
$Z_2$ is —$CR_h$—, where $R_h$ is —H, halogen or —CN;
$Z_3$ is —N—;
$Z_4$ is —$CR_j$—, where $R_j$ is —H, halogen or —CN; and
$Z_5$ is —$CR_k$—, where $R_k$ is —H, halogen or —CN.

2. The compound, the optical isomer, or the pharmaceutically acceptable salt of claim 1, wherein J is —N—; X is —N—; and $W_2$ is —$CR_e$—.

3. The compound, the optical isomer, or the pharmaceutically acceptable salt of claim 1, wherein Y is —CH—.

4. The compound, the optical isomer, or the pharmaceutically acceptable salt of claim 1, wherein J is —N—; X is —N—; $W_2$ is —$CR_e$—; Y is —CH—; and
$R_2$ is unsubstituted

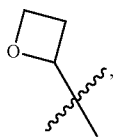 [SMILES: *C1CCO1]

halogen substituted

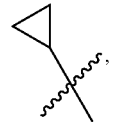

or unsubstituted

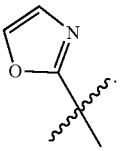 [SMILES: *c1ncco1]

5. The compound, the optical isomer, or the pharmaceutically acceptable salt of claim 1,
wherein $R_g$ is —H; $R_h$ is —H or halogen; $R_j$ is —H; and $R_k$ is —H, halogen or —CN.

6. The compound, the optical isomer, or the pharmaceutically acceptable salt of claim 4,
wherein $R_2$ is unsubstituted

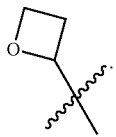 [SMILES: *C1CCO1]

7. The compound, the optical isomer, or the pharmaceutically acceptable salt of claim 1, wherein X is —N—.

8. The compound, the optical isomer, or the pharmaceutically acceptable salt of claim 1, wherein $W_2$ is —$CR_e$—.

9. The compound, the optical isomer, or the pharmaceutically acceptable salt of claim 1, wherein $R_h$ is —H or halogen; and $R_k$ is —H, halogen or —CN.

10. The compound, the optical isomer, or the pharmaceutically acceptable salt of claim 1, wherein $R_2$ is unsubstituted

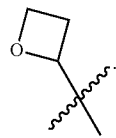

11. The compound, the optical isomer, or the pharmaceutically acceptable salt of claim 1,
wherein the compound represented by the Chemical Formula 1 is one selected from a group consisting of:
1-(oxazol-2-ylmethyl)-2-((4-(6-(pyridin-2-ylmethoxy)pyridin-2-yl)piperazin-1-yl)methyl)-1H-benzo[d]imidazole-6-carboxylic acid;
(S)-2-((4-(6-((5-chloro-3-fluoropyridin-2-yl)methoxy)pyridin-2-yl)piperazin-1-yl)methyl)-1-(oxetan-2-ylmethyl)-1H-benzo[d]imidazole-6-carboxylic acid;
(S)-2-((4-(6-((5-cyanopyridin-2-yl)methoxy)pyridin-2-yl)piperazin-1-yl)methyl)-1-(oxetane-2-ylmethyl)-1H-benzo[d]imidazole-6-carboxylic acid;
(S)-2-((4-(6-((5-cyanopyridin-2-yl)methoxy)pyrazin-2-yl)piperazin-1-yl)methyl)-1-(oxetane-2-ylmethyl)-1H-benzo[d]imidazole-6-carboxylic acid;
(S)-2-((4-(3-((5-cyanopyridin-2-yl)methoxy)phenyl)piperazin-1-yl)methyl)-1-(oxetan-2-ylmethyl)-1H-benzo[d]imidazole-6-carboxylic acid;
(S)-2-((4-(6-((5-cyanopyridin-2-yl)methoxy)pyridin-2-yl)piperazin-1-yl)methyl)-3-(oxetane-2-ylmethyl)-3H-imidazo[4,5-b]pyridin-5-carboxylic acid;
(S)-2-((4-(3-((5-cyanopyridin-2-yl)methoxy)phenyl)piperazin-1-yl)methyl)-3-(oxetane-2-ylmethyl)-3H-imidazo[4,5-b]pyridine-5-carboxylic acid;
(S)-2-((4-(6-((5-chloropyridin-2-yl)methoxy)pyridin-2-yl)piperazin-1-yl)methyl)-1-(oxetane-2-ylmethyl)-1H-benzo[d]imidazole-6-carboxylic acid;
2-(((S)-4-(6-((5-cyanopyridin-2-yl)methoxy)pyridin-2-yl)-2-methylpiperazin-1-yl)methyl)-1-(((S)-oxetan-2-yl)methyl)-1H-benzo[d]imidazole-6-carboxylic acid; and
2-(((S)-4-(6-((5-cyanopyridin-2-yl)methoxy)pyridin-2-yl)-2-methylpiperazin-1-yl)methyl)-3-(((S)-oxetan-2-yl)methyl)-3H-imidazo[4,5-b]pyridin-5-carboxylic acid.

12. The compound, the optical isomer, or the pharmaceutically acceptable salt of claim 11,
wherein the compound represented by the Chemical Formula 1 is one selected from a group consisting of:
(S)-2-((4-(6-((5-cyanopyridin-2-yl)methoxy)pyridin-2-yl)piperazin-1-yl)methyl)-1-(oxetane-2-ylmethyl)-1H-benzo[d]imidazole-6-carboxylic acid;
2-(((S)-4-(6-((5-cyanopyridin-2-yl)methoxy)pyridin-2-yl)-2-methylpiperazin-1-yl)methyl)-1-(((S)-oxetan-2-yl)methyl)-1H-benzo[d]imidazole-6-carboxylic acid;
1-(oxazol-2-ylmethyl)-2-((4-(6-(pyridin-2-ylmethoxy)pyridin-2-yl)piperazin-1-yl)methyl)-1H-benzo[d]imidazole-6-carboxylic acid;
(S)-2-((4-(6-((5-chloro-3-fluoropyridin-2-yl)methoxy)pyridin-2-yl)piperazin-1-yl)methyl)-1-(oxetan-2-ylmethyl)-1H-benzo[d]imidazole-6-carboxylic acid; and
(S)-2-((4-(6-((5-chloropyridin-2-yl)methoxy)pyridin-2-yl)piperazin-1-yl)methyl)-1-(oxetane-2-ylmethyl)-1H-benzo[d]imidazole-6-carboxylic acid.

13. A pharmaceutical composition for treating metabolic diseases comprising the compound, the optical isomer, or the pharmaceutically acceptable salt of claim 1, wherein the metabolic diseases are any one selected from the group consisting of diabetes, idiopathic T1D, latent autoimmune diabetes in adults (LADA), early onset T2DM (EOD), younger onset atypical diabetes (YOAD), maturity onset diabetes in young (MODY), malnutrition-related diabetes, gestational diabetes, hyperglycemia, insulin resistance, liver insulin resistance, impaired glucose tolerance, diabetic neuropathy, diabetic nephropathy, diabetic retinopathy, visceral fat accumulation, sleep apnea, obesity, eating disorders, dyslipidemia, hyperinsulinemia, non-alcoholic fatty liver disease (NAFLD), atherosclerosis, hypertension, congestive heart failure, myocardial infarction, stroke, hemorrhagic stroke, ischemic stroke, traumatic brain injury, pulmonary hypertension, restenosis after angioplasty, intermittent claudication, metabolic acidosis, ketosis, arthritis, osteoporosis, Parkinson© disease, left ventricular hypertrophy, peripheral arterial disease, loss of vision, cataracts, glomerulosclerosis, chronic renal failure, metabolic syndrome, X syndrome, premenstrual syndrome, angina, thrombosis, transient ischemic attack, vascular restenosis, symptoms of impaired fasting blood sugar, hyperuricemia, gout, erectile dysfunction, psoriasis, foot ulcers, ulcerative colitis, hyper-apo B lipoproteinemia, Alzheimer© disease, schizophrenia, cognitive impairment, inflammatory bowel disease, short bowel syndrome, Crohn[s] disease, colitis, irritable bowel syndrome and polycystic ovary syndrome.

14. The pharmaceutical composition for use of claim 13, wherein the non-alcoholic fatty liver disease is any one selected from the group consisting of steatosis, non-alcoholic steatohepatitis (NASH), fibrosis, cirrhosis, and hepatocellular carcinoma.

* * * * *

UNITED STATES PATENT AND TRADEMARK OFFICE
CERTIFICATE OF CORRECTION

| | |
|---|---|
| PATENT NO. | : 11,643,403 B2 |
| APPLICATION NO. | : 17/777193 |
| DATED | : May 9, 2023 |
| INVENTOR(S) | : Hong Chul Yoon et al. |

It is certified that error appears in the above-identified patent and that said Letters Patent is hereby corrected as shown below:

In the Claims

At Column 61, Line 17, "Parkinson© disease," should be -- Parkinson's disease, --.

At Column 62, Line 7, "Alzheimer© disease," should be -- Alzheimer's disease, --.

At Column 62, Line 9, "Crohn|š| disease," should be -- Crohn's disease, --.

Signed and Sealed this
Nineteenth Day of December, 2023

*Katherine Kelly Vidal*

Katherine Kelly Vidal
*Director of the United States Patent and Trademark Office*